United States Patent
Oda

(10) Patent No.: US 9,550,026 B2
(45) Date of Patent: Jan. 24, 2017

(54) SYRINGE

(75) Inventor: Shingo Oda, Tatsuno (JP)

(73) Assignee: DAICEL CORPORATION, Osaka (JP)

( * ) Notice: Subject to any disclaimer, the term of this patent is extended or adjusted under 35 U.S.C. 154(b) by 25 days.

(21) Appl. No.: 13/825,780

(22) PCT Filed: Sep. 22, 2011

(86) PCT No.: PCT/JP2011/071624
§ 371 (c)(1),
(2), (4) Date: May 30, 2013

(87) PCT Pub. No.: WO2012/039458
PCT Pub. Date: Mar. 29, 2012

(65) Prior Publication Data
US 2014/0200512 A1  Jul. 17, 2014
US 2015/0057607 A9  Feb. 26, 2015

(30) Foreign Application Priority Data
Sep. 24, 2010  (JP) .................. 2010-214541

(51) Int. Cl.
*A61M 5/30* (2006.01)
*A61M 5/20* (2006.01)

(52) U.S. Cl.
CPC ............. *A61M 5/30* (2013.01); *A61M 5/2046* (2013.01)

(58) Field of Classification Search
CPC .............................. A61M 5/2046; A61M 5/30
(Continued)

(56) References Cited

U.S. PATENT DOCUMENTS 2,704,542 A   3/1955  Scherer
6,837,866 B1  1/2005  Alexandre et al.
(Continued)

FOREIGN PATENT DOCUMENTS

CN   1436088 A    8/2003
JP   2003520073   7/2003
(Continued)

OTHER PUBLICATIONS

Extended European Search Report for International Application No. PCT/JP2011/071624 dated Jan. 24, 2014 by the European Patent Office.
(Continued)

*Primary Examiner* — Theodore Stigell
*Assistant Examiner* — Tiffany Legette
(74) *Attorney, Agent, or Firm* — Knobbe Martens Olson & Bear LLP

(57) ABSTRACT

It is possible to feed an injection objective substance to a depth of a skin structure of an objective living body without using any injection needle. A syringe having no injection needle comprises an ignition device which includes an ignition charge containing a fuel component and an oxidizing agent component, a combustion chamber into which a combustion product produced by a reaction of the fuel component and the oxidizing agent component during combustion of the ignition charge is allowed to flow and which accommodates a gas generating agent that is combustible by the combustion product to generate a predetermined gas, and an enclosing unit which encloses the injection objective substance, wherein the injection objective substance enclosed in the enclosing unit is pressurized by a pressure in the combustion chamber in this construction. The fuel component and the oxidizing agent component contained in the ignition charge are determined so that any component, (Continued)

which behaves as a gas, is excluded from the combustion product when the combustion product is at ordinary temperature in the case where the fuel component and the oxidizing agent component are mixed at a stoichiometric ratio and combusted, and a cooling member is arranged in the combustion chamber so that the cooling member can be brought in contact with the combustion product produced by the combustion of the ignition charge to cool the combustion product.

6 Claims, 9 Drawing Sheets

(58) Field of Classification Search
USPC .......... 604/48, 68, 69, 140–148; 128/203.26
See application file for complete search history.

(56) References Cited

U.S. PATENT DOCUMENTS

| | | | | |
|---|---|---|---|---|
| 6,913,593 | B1* | 7/2005 | Alexandre | A61M 5/3015 604/48 |
| 7,150,409 | B2 | 12/2006 | Gonnelli et al. | |
| 7,931,614 | B2 | 4/2011 | Gonnelli et al. | |
| 2001/0037810 | A1* | 11/2001 | Fine | A61K 33/00 128/203.26 |
| 2002/0004639 | A1 | 1/2002 | Willis et al. | |
| 2002/0151842 | A1 | 10/2002 | Gonnelli et al. | |
| 2002/0156418 | A1 | 10/2002 | Gonnelli et al. | |
| 2002/0161329 | A1 | 10/2002 | Gonnelli et al. | |
| 2003/0114789 | A1 | 6/2003 | Haar et al. | |
| 2003/0135155 | A1 | 7/2003 | Alexandre et al. | |
| 2003/0149397 | A9 | 8/2003 | Gonnelli et al. | |
| 2004/0049151 | A1 | 3/2004 | Lell et al. | |
| 2004/0220525 | A1* | 11/2004 | Willis et al. | 604/141 |
| 2004/0225025 | A1* | 11/2004 | Sullivan | C08G 59/62 522/71 |
| 2005/0010167 | A1 | 1/2005 | Alexandre et al. | |
| 2005/0010168 | A1 | 1/2005 | Kendall | |
| 2006/0258986 | A1 | 11/2006 | Hunter et al. | |
| 2008/0071192 | A1* | 3/2008 | Hynes | A61B 10/025 600/562 |
| 2008/0071211 | A1* | 3/2008 | Williamson | A61M 5/30 604/68 |
| 2009/0044885 | A1* | 2/2009 | Brisighella | C06B 45/00 149/18 |
| 2011/0172634 | A1 | 7/2011 | Gonnelli et al. | |

FOREIGN PATENT DOCUMENTS

| | | |
|---|---|---|
| JP | 2003534839 | 11/2003 |
| JP | 2005511254 | 4/2005 |
| JP | 2008220980 | 9/2008 |

OTHER PUBLICATIONS

International Preliminary Report on Patentability in International Application No. PCT/JP2011/071624 dated Apr. 16, 2013.

Joy Baxter, Samir Mitragotri, "Jet-induced skin puncture and its impact on needle-free jet injections: Experimental studies and a predictive model". Journal of Controlled Release (U.S.A.) 106(2005), p. 361-373.

Joy Schramm-Baxter, Samir Mitragotri, "Needle-free jet injections: dependence of jet penetration and dispersion in the skin on jet power", Journal of Controlled Release (U.S.A.) 97(2004), p. 527-535.

Chinese Office Action recieved on Jul. 9, 2014 for corresponding Chinese Application No. 201180056573.0.

* cited by examiner (a)

(b)

(a)

(b)

SYRINGE

TECHNICAL FIELD

The present invention relates to a syringe (injector) with which an injection objective substance is injected into an injection target area of a living body without using any injection needle.

BACKGROUND ART

In relation to a needle-free syringe (needleless syringe) with which the injection is performed without using any injection needle, a construction is adopted in some cases such that an injection component is injected or allowed to inject by applying a pressure to an accommodating chamber in which an injection solution is accommodated, by means of a pressurized gas or a spring. However, in the case of the needle-free syringe having the conventionally known construction, the reproducibility is unsatisfactory in relation to the depth and the injection amount of the injection solution. Therefore, it is difficult to affirm that such a needle-free syringe generally comes into widespread use.

Accordingly, such a technique is disclosed that a propellant charge, which is composed of a mixture of two types of powders, i.e., a high speed combustion powder and a low speed combustion powder, is utilized to adjust the output pressure (injection pressure) for the injection solution in a plurality of levels or stages (see, for example, Patent Document 1). Specifically, the injection solution is firstly allowed to inject by applying a large force to a piston by the combustion of the high speed combustion powder. As a result, the injection solution penetrates through a skin of a human body or the like, and the injection solution is fed into the body. After that, a pressure is continuously applied to such an extent that the injection solution can be diffused in the skin by the combustion of the low speed combustion powder. Patent Document 2 discloses such a technique that an injection solution is administered in two stages by using a needle-free syringe. In this technique, the injection solution is allowed to inject by applying a high pressure thereto so that the injection solution penetrates into the skin, and then the pressure, which is applied to the injection solution, is lowered so that it is contemplated to disperse the injection solution in the skin. Further, Patent Document 3 discloses such a technique that the injection pressure for an injection solution is adjusted by the intensity of the electric current by using a magnet and a coil. In this technique, the injection pressure is adjusted so that a high pressure is firstly applied in order that the injection solution penetrates through the skin, and then an approximately constant pressure is provided in order that the desired injection solution is fed or delivered.

In this context, Patent Document 3 discloses such a technique that an inactive or inert material is provided in a combustion chamber in which an explosive charge (a propellant charge) is combusted in order that the heat, which is generated from the explosive charge, is temporarily stored, in a needle-free syringe which uses the explosive charge in order to adjust the injection pressure for an injection solution. According to this technique, when the combustion of the explosive charge is completed, then the heat, which is possessed by the combustion gas generated in the combustion, is temporarily stored in the inert material, and then the heat is given and received between the inert material and the combustion gas. Accordingly, it is intended to maintain the gas temperature and the pressure in the combustion chamber. However, the composition of the explosive charge is not disclosed specifically and sufficiently. On the other hand, Patent Document 4 discloses specified examples of explosive charges components of an ignition charge and a propellant which are assumed to be usable in a needle-free syringe. For example, $BKNO_3$ (boron/potassium nitrate) is exemplified as the ignition charge, and $CuO$/5-aminotetrazole is exemplified as the propellant.

A mode or form for allowing an injection solution to inject by any means other than the explosive charges is also known, as Patent Document 5 discloses such a technique that the injection pressure for the injection solution is adjusted by the intensity of, the electric current by using a magnet and a coil. In this technique, the injection pressure is adjusted such that a high pressure is firstly applied in order to penetrate through the skin, and then an approximately constant pressure is provided in order that the desired injection solution is fed or delivered.

The pressure, which is applied to the injection solution when the needle-free syringe is used, is variously adjusted not only for such a purpose that the injection solution is allowed to arrive at the interior of the skin but also for other purposes other than the above. For example, in Patent Document 6, such a description is found that the increase in the pressure applied to the injection solution is unfavorable after the penetration through the skin in order to mitigate the noise generated when the injection solution is allowed to inject by using a pressurized gas.

In this context, the target, for which the injection is performed by using the needle-free syringe, is the living body such as the human body or the like in many cases. Accordingly, a discussion is provided in relation to the behavior of an injected solution with respect to a gel agent generally used for an experiment and the skin of the living body (see, for example, Non-Patent Document 1). This discussion refers, for example, to a correlation between a depth of a hole formed by the injection and a hole depth having a maximum dispersion width, and a correlation between the Young's modulus of the skin and the hole depth. Further, Non-Patent Document 2 refers to a correlation between the dispersion width of an injection solution in the human skin and the nozzle diameter of a needle-free syringe.

PRECEDING TECHNICAL DOCUMENTS

Patent Documents

Patent Document 1: JP2003-534839;
Patent Document 2: U.S. Pat. No. 2,704,542;
Patent Document 3: JP2005-511254;
Patent Document 4: JP2008-220980;
Patent Document 5: United States Patent Publication No. 2006/0258986;
Patent Document 6: United States Patent Publication No. 2005/0010168.

Non-Patent Documents

Non-Patent Document 1: Joy Baxter, Samir Mitragotri, "Jet-induced skin puncture and its impact on needle-free jet injections: Experimental studies and a predictive model", Journal of Controlled Release (U.S.A.) 106 (2005), p 361-373;
Non-Patent Document 2: Joy Schramm-Baxter, Samir Mitragotri, "Needle-free jet injections: dependence of jet penetration and dispersion in the skin on jet power", Journal of Controlled Release (U.S.A.) 97 (2004), p 527-535.

SUMMARY OF THE INVENTION

Problem to be Solved by the Invention

When the injection is performed for the living body, the component which is contained in the injection solution and the depth in the injection target area of the living body into which the component is to be fed differ depending on the purpose of the injection. This is because the injection target area of the living body includes various structures such as skin, muscle, internal organs and the like, and the biological tissues, which constitute the structures, have different functions depending on the depths from the surface (surface on which the syringe is brought in contact with the structure when the injection is performed), and because it becomes difficult to appropriately exhibit the effect if the component contained in the injection solution does not arrive at the objective biological tissue.

For example, the human skin can be distinguished or classified into epidermis, dermis, and subcutaneous tissue (hypodermis) in a layered form from the surface side. Further, the epidermis can be distinguished or classified into horny cell layer and intradermis. In order that the respective layers perform the respective functions anatomically, the horny cell layer is composed of keratinocytes, the intradermis is composed of dendritic cells and pigment cells, the dermis is composed of fibroblasts and collagen cells, and the subcutaneous tissue is composed of subcutaneous fat and the like. When an injection solution is injected for a predetermined purpose, it is preferable that the predetermined component contained therein is precisely delivered, for example, to the objective tissue.

In order that the injection objective substance is efficiently injected without a leakage when the injection objective substance is injected into the injection target area of the living body, it is necessary that the pressure, which is applied to the injection objective substance, should be appropriately controlled. That is, if the injection speed (velocity) of the injection objective substance, which is brought about by the pressurization, is too slow, the substance is rebounded by the skin. To the contrary, if the injection speed (velocity) is too fast, then the injection depth can be secured in the injection target area, but the injection speed exceeds an injection speed which is adequate to diffuse the substance in the area. Therefore, it is considered that the injection objective substance is rebounded due to the excessive supply, and it is difficult to contemplate the appropriate diffusion thereof. In particular, at the initial stage of the injection of the injection solution, it is necessary that the injection solution should be allowed to penetrate through the surface of the injection target area of the living body to form a state which is favorable for the injection solution to be diffused into the interior thereof (hereinafter referred to as "diffusion preparatory state" as well). Therefore, it is considered that the pressure control, which is performed at the initial stage of the injection, is extremely important. Taking the foregoing problem into consideration, an object of the present invention is to provide a syringe which makes it possible to feed an injection objective substance into an objective injection target area of a living body without using any injection needle so that the injection objective substance can be widely diffused at a depth.

Solution for the Problem

In order to solve the problem as described above, the present invention adopts the following construction. That is, the pressure source of the pressurizing force to be exerted on an injection objective substance is an ignition charge having specified components and a gas generating agent, and the pressure transition brought about by the ignition charge is made steep as far as possible, in relation to a syringe for injecting the injection objective substance into an injection target area of a living body without using any injection needle. Owing to the adoption of the ignition charge and the gas generating agent and the adoption of the pressure transition of the ignition charge, the injection objective substance can be fed into a biological tissue at a wide range of depths including relatively shallow depths in the injection target area.

Specifically, the present invention provides a syringe for injecting an injection objective substance into an injection target area of a living body without using any injection needle; the syringe including an ignition device which includes an ignition charge containing a fuel component and an oxidizing agent component; a combustion chamber into which a combustion product produced by a reaction of the fuel component and the oxidizing agent component during combustion of the ignition charge is allowed to flow and which accommodates a gas generating agent that is combustible by the combustion product to generate a predetermined gas; an enclosing unit which encloses the injection objective substance; a pressurizing unit which is constructed to pressurize the injection objective substance enclosed in the enclosing unit by means of a pressure in the combustion chamber; and a flow passage unit which defines a flow passage so that the injection objective substance, which is pressurized by the pressurizing unit, is allowed to inject to the injection target area of the living body. Further, the fuel component and the oxidizing agent component contained in the ignition charge are determined so that any component, which behaves as a gas, is excluded from the combustion product when the combustion product is at ordinary temperature in the case where the fuel component and the oxidizing agent component are mixed at a stoichiometric ratio and combusted; and a cooling member is arranged in the combustion chamber so that the cooling member can be brought in contact with the combustion product produced by the combustion of the ignition charge to cool the combustion product.

In the syringe according to the present invention, the injection objective substance, which is to be injected into the injection target area of the living body, is enclosed in the enclosing unit, and the pressure is applied to the injection objective substance enclosed in the enclosing unit. Thus, the movement of the injection objective substance is prompted. As a result, the injection objective substance is allowed to discharge to the injection target area while passing through the flow passage unit. The injection objective substance contains a component or ingredient which is expected to exhibit any efficacy at the inside of the injection target area. In this context, the syringe according to the present invention is constructed such that the enclosed injection objective substance is pressurized by the pressure which is brought about in the combustion chamber by the combustion product and the predetermined gas generated by the combustion of the ignition charge possessed by the ignition device and the gas generating agent accommodated in the combustion chamber respectively. In other words, the pressure transition, which is provided in the combustion chamber by the combustion product and the predetermined gas, is the driving source when the injection objective substance is allowed to inject. Therefore, any enclosing state of the injection objective substance in the enclosing unit or any physical form for the injection objective substance such as liquid, fluid in a gel form, powder, solid in a granular form in the enclosing unit is available as long as the injection objective substance can be allowed to inject by being pressurized in the pressurizing unit.

For example, the injection objective substance may be a liquid or solid in a gel form, provided that the fluidity, which makes it possible to allow the injection objective substance to inject, is secured or guaranteed. Further, the component, which is to be fed into the injection target area of the living body, is contained in the injection objective substance. The component may exist in such a state that the component is dissolved in the injection objective substance, or the component may be in such a state that the component is simply mixed without being dissolved. For example, the component to be fed includes, for example, vaccine for enhancing antibody, protein for beauty, and cultured cells for regenerating hair. The injection objective substance is formed by containing the component in a liquid or a fluid in a gel form or the like so that the component as described above can be allowed to inject.

In this context, the fuel component and the oxidizing agent component, which are subjected to the combustion reaction of the ignition charge, are specifically determined so that any component, which behaves as the gas, is theoretically excluded from the combustion product when the combustion product is at ordinary temperature in the case where the components are mixed at the stoichiometric ratio and combusted. That is, the fuel component and the oxidizing agent component of the ignition charge are determined so that any component, which behaves as the gas, is not contained in the combustion product upon the arrival at ordinary temperature as the temperature of the combustion product is lowered in accordance with the elapse of time (even in a short period of time), even if any component, which behaves as the gas, is contained in the combustion product, because the temperature is relatively high immediately after the both components are subjected to the combustion reaction. In other words, the fuel component and the oxidizing agent component of the ignition charge are determined so that any component, which is the gas at the high temperature, is changed to the solid or the liquid at ordinary temperature. The phrase "mixed at a stoichiometric ratio and combusted" referred to herein means such a situation that the oxidizing agent component is consumed neither too much nor too little with respect to the fuel component to cause the combustion. Therefore, for example, in the case of a situation in which the amount of the actual oxidizing agent component is larger with respect to the amount of the fuel component and which may be realistically caused, oxygen, which is produced from the oxidizing agent component itself, remains as an unreacted substance. However, such a situation falls under the case in which "the fuel component and the oxidizing agent component contained in the ignition charge are determined so that any component, which behaves as a gas, is excluded from the combustion product when the combustion product is at ordinary temperature in the case where the fuel component and the oxidizing agent component are mixed at a stoichiometric ratio and combusted", provided that the fuel component and the oxidizing agent component are used, for which any composition ratio is present so that any component, which behaves as a gas at ordinary temperature, is not contained in the combustion product produced by the reaction of the both components.

The term "ordinary temperature" referred to herein is the temperature which is low to such an extent that the temperature can be distinctly distinguished from the high temperature which is provided immediately after the combustion reaction of the fuel component and the oxidizing agent component in the combustion chamber. The temperature belongs to a range at which the combustion product of the ignition charge allowed to flow into the combustion chamber can reach in any situation in which the use of the syringe according to the present invention is assumed. Therefore, it can be understood that the ordinary temperature according to the present invention provides a concept having a relatively wide temperature range.

On the other hand, the ignition charge may Contain an additive component which is added in order to achieve a predetermined object in addition to the fuel component and the oxidizing agent component described above. For example, the ignition charge may contain, as the additive component, a combustion adjusting agent which is used to adjust the combustion state of the fuel component or a binder or the like which is generally used to form the ignition charge. Even when the ignition charge contains the additive component, and any gas may be produced resulting from the additive component (for example, carbon dioxide produced by the combustion of the binder), then it is acknowledged that the ignition charge is usable for the syringe according to the present invention, on condition that both of the fuel component and the oxidizing agent component are determined so that "any component, which behaves as a gas, is excluded from the combustion product when the combustion product is at ordinary temperature in the case where the fuel component and the oxidizing agent component are mixed at a stoichiometric ratio and combusted" as described above, in relation to the fuel component and the oxidizing agent component thereof.

For example, it is possible to adopt, as the ignition charge described above, any one of explosive charges of an explosive charge containing zirconium and potassium perchlorate, an explosive charge containing titanium hydride and potassium perchlorate, an explosive charge containing titanium and potassium perchlorate, an explosive charge containing aluminum and potassium perchlorate, an explosive charge containing aluminum and bismuth oxide, an explosive charge containing aluminum and molybdenum oxide, an explosive charge containing aluminum and copper oxide, and an explosive charge containing aluminum and iron oxide, or an explosive charge composed of a combination of a plurality of the foregoing explosive charges.

For example, in the case of $BKNO_3$ (boron/potassium nitrate) disclosed in Patent Document 4, boron oxide ($B_2O_3$), potassium oxide ($K_2O$), and nitrogen ($N_2$) are produced when the combustion occurs. Therefore, it is evident that gaseous nitrogen is contained at ordinary temperature. However, for example, when the mixture (ZPP) of zirconium and potassium perchlorate is used as the ignition charge to be used for the syringe of the present invention, then the substances, which are produced by the combustion, are only zirconium oxide and potassium chloride in view of the stoichiometry, and no gas component is contained at ordinary temperature. Further, the ignition charge containing titanium hydride and potassium perchlorate produces titanium oxide, potassium chloride, and water, and the ignition charge containing titanium and potassium perchlorate produces titanium oxide and potassium chloride. Aluminum oxide and potassium chloride are produced from the ignition charge containing aluminum and potassium perchlorate, aluminum oxide and bismuth are produced from the ignition charge containing aluminum and bismuth oxide, aluminum oxide and molybdenum are produced from the ignition charge containing aluminum and molybdenum oxide, aluminum oxide and copper are produced from the ignition charge containing aluminum and copper oxide, and aluminum oxide and iron are produced from the ignition charge containing aluminum and iron oxide, wherein it is appreciated that any component, which is a gas at ordinary temperature, is not contained. The foregoing description has been made by way of example. Any component, which does not contain any gas at ordinary temperature in the same manner as described above, can provide the effect of the present invention.

When the ignition charge, which produces the combustion product containing no gas component at ordinary temperature, is utilized as described above, the relatively high pressure is applied to the injection objective substance immediately after the ignition of the ignition charge at the initial stage of the pressurization in the pressurizing unit in order to allow the injection objective substance to inject. Further, the combustion product thereafter reaches such a state that no gas is contained (i.e., the combustion product is changed to liquid or solid by being cooled), and thus the pressure in the combustion chamber can be suddenly lowered. The syringe according to the present invention includes the cooling member which is arranged at the position at which the combustion product can be brought in contact therewith. Therefore, the combustion product is quickly subjected to the transition to ordinary temperature by the cooling action of the cooling member. Therefore, the period of time, which ranges to the arrival of the temperature of the combustion product at ordinary temperature immediately after the ignition of the ignition charge, can be within an extremely short period of time at the initial stage of the pressurization executed in the syringe according to the present invention.

The initial stage of the pressurization in the pressurizing unit is such a stage that the injection solution is allowed to penetrate through the surface of the injection target area of the living body to form the diffusion preparatory state as the state preferable for the injection solution to be diffused to the inside thereof. After undergoing the diffusion preparatory state, the injection objective substance is progressively diffused into the inside of the injection target area by the pressurization brought about by the predetermined gas generated from the gas generating agent. The quick decrease in the temperature of the combustion product produced from the ignition charge, which is caused at the initial stage of the pressurization in the pressurizing unit, is extremely useful to widen the range of adjustment of the injection depth in the injection target area. In particular, when it is intended to diffuse the injection objective substance to a relatively shallow portion of the injection target area, it is preferable that the period of time, which is required for the combustion product to arrive at ordinary temperature, is short as far as possible.

It is also preferable that the syringe as described above is constructed such that the pressurizing unit has a first pressurizing mode in which a pressure applied to the injection objective substance in the pressurizing unit is raised to a first peak pressure in order to allow the injection objective substance to penetrate through a surface of the injection target area, and then the pressure applied to the injection objective substance is lowered to a waiting pressure; and a second pressurizing mode in which the injection objective substance having the waiting pressure is pressurized so that the pressure applied to the injection objective substance is raised to a second peak pressure to inject a predetermined injection amount of the injection objective substance.

The injection objective substance can be more preferably injected into the injection target area of the living body owing to the two pressurizing modes possessed by the pressurizing unit as described above. In other words, when the first pressurizing mode and the second pressurizing mode are adopted, then the injection objective substance is fed to the objective injection depth of the injection target area such as the skin structure or the like, and the injection objective substance is diffused. In the first pressurizing mode, the pressure applied to the injection objective substance is raised to the first peak pressure, and then the pressure is lowered to the waiting pressure. Accordingly, the injection objective substance firstly penetrates through the surface of the injection target area of the living body, and the injection objective substance advances in the depth direction of the area.

The injection energy of the injection objective substance is determined by the flow rate of the substance allowed to inject per unit time. Therefore, the larger the pressurizing speed (velocity) for the injection objective substance (amount of pressure increase per unit time) in the first pressurizing mode is, the deeper the injection depth brought about by the injection objective substance in the first pressurizing mode is. In the first pressurizing mode, the pressure increase is adjusted so that at least the pressure, which is required to penetrate through the surface of the injection target area, is applied to the injection objective substance.

In this context, the applicant assumes the following mechanism for the injection into the injection target area, of the injection objective substance allowed to inject. It is not intended that the present applicant is restricted by this mechanism. It is considered that any other invention, which provides the effect that is the same as or equivalent to the effect of the present application as a result of the execution of the pressure control with respect to the injection objective substance as described in the present application, belongs to the category of the present invention, even if the other invention follows any mechanism different from the mechanism.

When the injection objective substance is allowed to discharge to the injection target area, then the forward end of the flow (jet flow) of the pressurized injection objective substance allowed to discharge at the early stage cuts out the injection target area, and the cut fragments are lifted upwardly by the back flow. Accordingly, a hole is bored, and the forward end of the jet flow advances in the depth direction. As the forward end of the jet flow is deepened, the injection energy, which is possessed by the jet flow, is lost by the friction with the back flow. When the injection energy is lost by the back flow, and the ability to cut out the injection target area is lost, i.e., when the injection energy is balanced with the resistance energy of the back flow, then the advance of the hole depth is stopped.

When the jet flow is provided into the injection target area, the same amount of the back flow comes upwardly in the opposite direction in the hole. Therefore, it is necessary that the hole diameter should be secured in order to allow the back flow to flow therethrough. However, the biological tissue, which is the injection target area, intrinsically has the elasticity, and hence the biological tissue has such a tendency that the biological tissue is contracted or shrunk to decrease the hole diameter. The contractile force (shrinkage force) narrows the back flow passage (reduces the diameter). Therefore, when such a state is given that the contractile force is relatively large with respect to the jet flow, then the resistance, which is brought about by the back flow, is increased, and the injection energy possessed by the jet flow is balanced at a relatively shallow position.

Taking the foregoing mechanism into consideration, the present invention is considered as follows. That is when the pressure, which is applied to the injection objective substance, is raised to the first peak pressure, and the pressure is thereafter lowered to the waiting pressure, then the elastic force, which is intrinsically possessed by the injection target area of the living body, is relatively large as compared with the jet flow at a part of the penetrating passage (forward end portion of the penetrating passage) of the injection objective substance formed to arrive at a certain injection depth. Therefore, it is considered that the diameter of the penetrating passage is reduced. In this situation, it is considered that the forward end portion of the injection objective substance that is subjected to the pressure reduction to the waiting pressure, is in such a state that the pressure (waiting pressure) applied to the injection objective substance is generally balanced with the pressure brought about by the back flow from the injection target area of the living body, at such a position that the injection target area of the living body, which is positioned at the forward end portion of the penetrating passage having the reduced diameter, is not reached. It is considered that when the diameter is reduced at the part of the penetrating passage as described above, the strength against the jet flow is raised as compared with any portion which is not subjected to the reduction of the diameter. The increase in the strength means that it is difficult to secure the back flow route when the pressurization is performed again in the second pressurizing mode. Therefore, even when the pressurization is performed again in accordance with the second pressurizing mode after the arrival at the waiting pressure, the jet flow does not reach the forward end of the penetrating passage, because the area, through which the back flow passes, is lost in the contracted or shrunk penetrating passage, wherein the pressurization is principally effected for the injection objective substance existing in the portion of the penetrating passage not subjected to the diameter reduction. Therefore, the permeation of the injection objective substance is facilitated in the direction in which the injection objective substance is spread in the injection area of the living body, rather than the penetrating passage is further elongated in the depth direction. Thus, the injection objective substance is diffused in a wide range. In a way, it is also affirmed that the first pressurizing mode, which is provided until arrival at the waiting pressure, is the step which makes it possible to form such a state that the diffusion is to be performed, and the second pressurizing mode is the step which accelerates the diffusion of the injection objective substance in the formed state. In the second pressurizing mode, the pressure applied to the injection objective substance is raised to the second peak pressure, and thus it is possible to realize the injection of the injection objective substance in an objective predetermined injection amount.

The first peak pressure and the waiting pressure in the first pressurizing mode described above and the second peak pressure in the second pressurizing mode are appropriately determined depending on the purpose of the injection of the injection objective substance. In this context, it is also appropriate to consider the physical property of the injection target area of the living body as the target, for example, the Young's modulus or the like of the skin. The living body, which is the injection target of the syringe according to the present invention, is not limited to human, which may be, for example, a farm animal such as pig or a pet such as dog.

As described above, according to the syringe of the present invention, the cooling member is adopted, which prompts the quick decrease in the temperature of the combustion product produced from the ignition charge containing no gas component in the combustion product at ordinary temperature when the ignition charge is mixed at the stoichiometric ratio and combusted. Thus, it is possible to shorten the period of time required until the pressure arrives at the waiting pressure from the ignition of the ignition charge. Further, the injection objective substance undergoes the waiting pressure when the mode transitions from the first pressurizing mode to the second pressurizing mode. Thus, it is possible to effectively contemplate the diffusion of the injection objective substance in the injection target area without uselessly deepening the injection depth. It is understood that the syringe according to the present invention is useful in order to diffuse the injection objective substance to the shallower portion of the injection target area.

In the syringe as described above, it is also preferable that the waiting pressure is not more than a first predetermined ratio of the first peak pressure. The present applicant found out the fact that the effective diffusion of the injection objective substance as described above can be realized when the ratio of the waiting pressure with respect to the first peak pressure is not more than the first predetermined ratio. Preferably, for example, the first predetermined ratio is set to 60%.

In the syringe as described above, the cooling member may be formed of a material made of metal. In general, the material made of metal has a large heat capacity (thermal capacity), and hence the material made of metal is the material preferable to form the cooling member. As an example of the cooling member, it is also preferable to adopt such a construction that the cooling member is arranged along a side wall of the combustion chamber positioned in a direction in which the combustion product flows into the combustion chamber. When the cooling member is arranged along the side wall of the combustion chamber as described above, then it is possible to increase the substantial contact area between the cooling member and the combustion product allowed to flow into the combustion chamber, and it is possible to realize the more effective cooling of the combustion product. In this arrangement, when the cooling member is provided with a plurality of through-holes, it is possible to expect the more excellent cooling effect.

As another example of the cooling member, it is also preferable that the cooling member is a metal member which is arranged in the combustion chamber. Further, it is also preferable that the metal member is provided so that the pressure, which is brought about by the predetermined gas and the combustion product produced in the combustion chamber, is transmitted to the injection objective substance. That is, the cooling member of the present invention is arranged as a block-shaped metal member in the combustion chamber, and thus the cooling member functions to substantially decrease the volume of the combustion chamber. Therefore, the pressure in the combustion chamber can be instantaneously raised by the operation of the ignition device, and the energy, which is supplied from the ignition device, can be efficiently used to raise the pressure in the combustion chamber. Owing to the fact that the cooling member is formed of the metal material, it is possible to secure the larger amount of heat which can be deprived from the combustion product. Therefore, it is possible to expect the quick decrease in the temperature of the combustion product. Further, the metal member is also brought in contact with the predetermined gas generated by the combustion of the gas generating agent. However, this contact occurs after the combustion product has been already brought in contact. Therefore, the thermal energy (heat energy) of the predetermined gas is prevented from being deprived by the metal member in a large amount. Therefore, the pressurization for the injection objective substance, which is effected by the predetermined gas, is performed relatively efficiently.

Effect of the Invention

It is possible to feed the injection objective substance to the depth of the objective injection target area of the living body without using any injection needle so that the injection objective substance can be widely diffused at the depth brought about thereby.

MODE FOR CARRYING OUT THE INVENTION

A syringe 1 according to an embodiment of the present invention will be explained below with reference to the drawings. The construction of the following embodiment is described by way of example. The present invention is not limited to the construction of the embodiment.

Figure 1A:
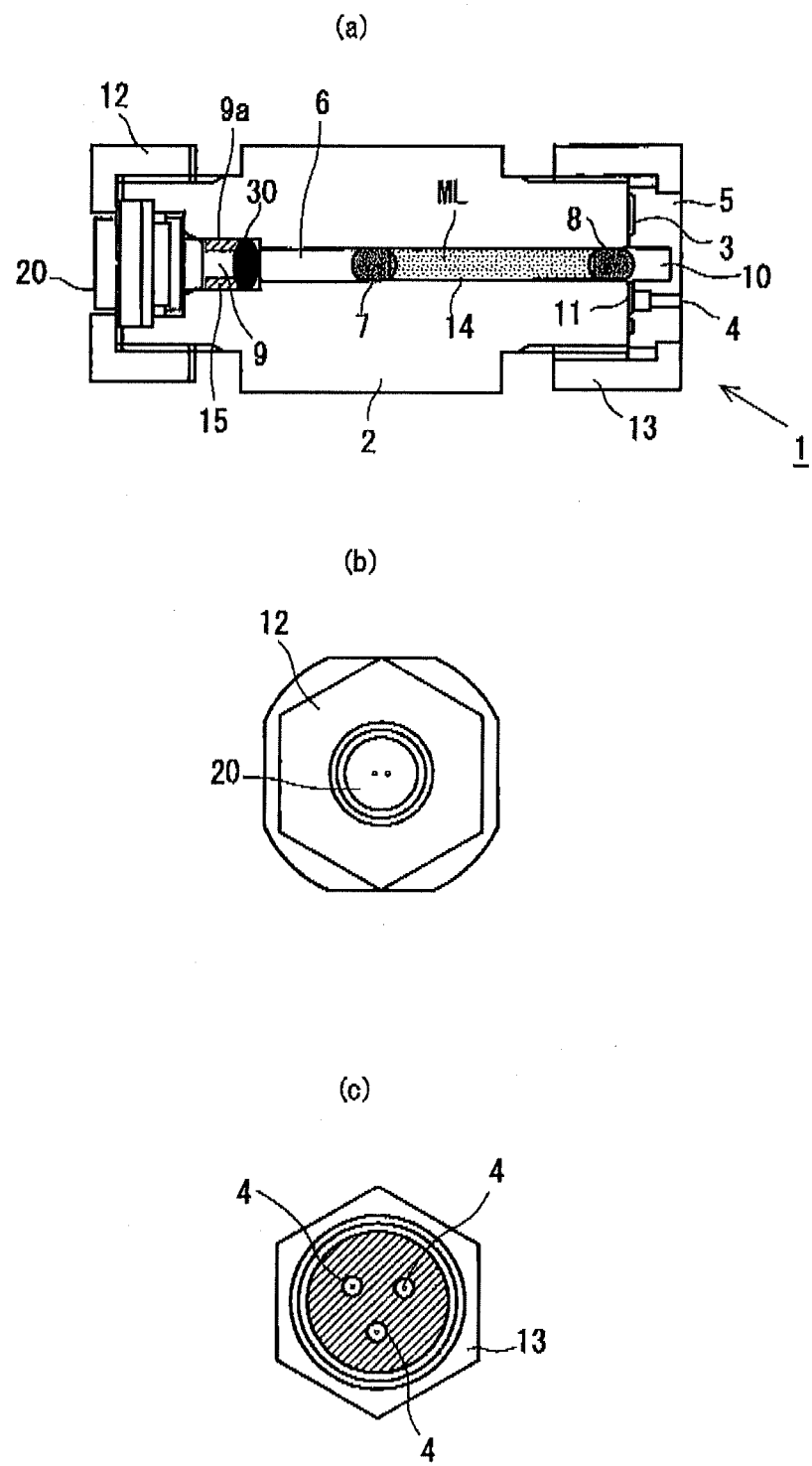
FIG. 1A shows a schematic arrangement of a syringe according to the present invention.
Figure 1B:
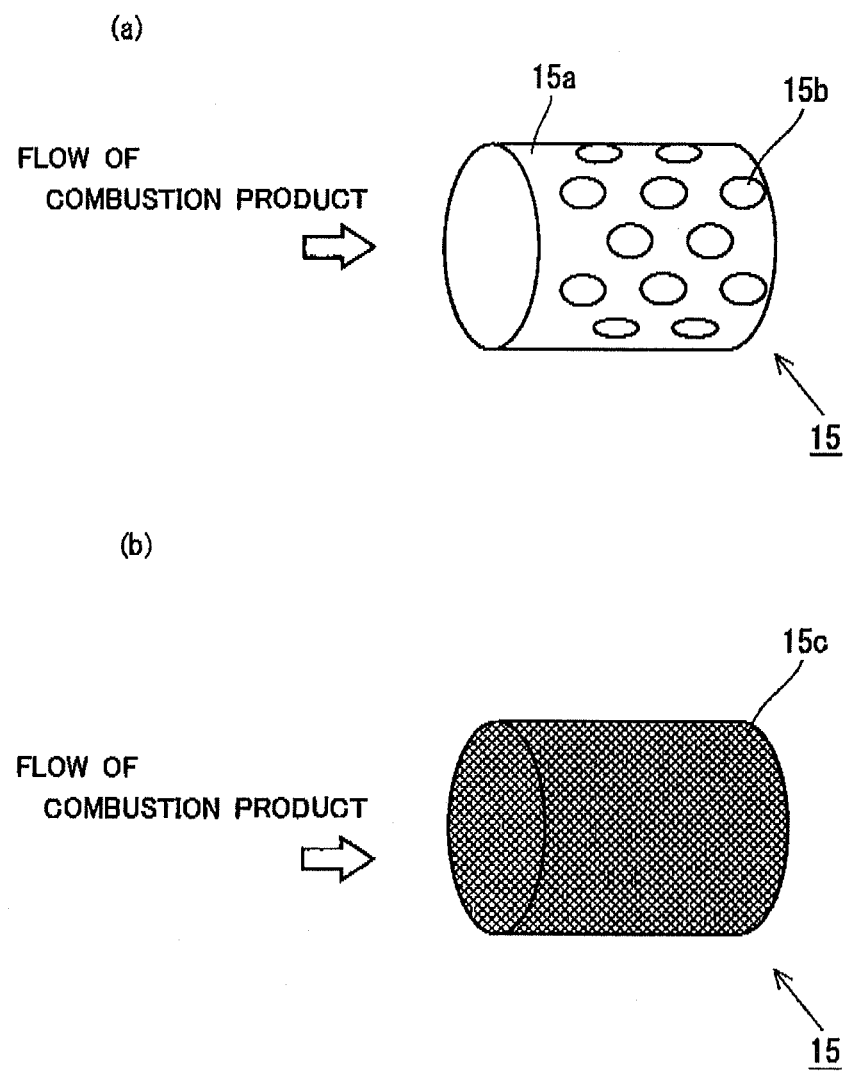
FIG. 1B shows schematic arrangements of cooling members to be arranged in the syringe shown in FIG. 1A.

In this embodiment, FIGS. 1A and 1B show the schematic arrangement of the syringe 1 according to the present invention. At first, FIG. 1A(a) shows a sectional view illustrating the syringe 1, FIG. 1A(b) shows a side view illustrating the syringe 1 as viewed from a side of an initiator 20, and FIG. 1A(c) shows a side view illustrating the syringe 1 as viewed from a side of nozzles 4 for allowing an injection solution to inject. In the next place, FIG. 1B shows, in FIG. 1BA and FIG. 1BB respectively, two specified forms of cooling members 15 arranged in a combustion chamber 9 of the syringe 1 as described later on. The syringe 1 has a main syringe body 2. A through-hole 14, which extends in the axial direction and which has a constant diameter in the axial direction, is provided at a central portion of the main syringe body 2. One end of the through-hole 14 is communicated with a combustion chamber 9 which has a diameter that is larger than the diameter of the through-hole 14. The remaining other end reaches the side of a nozzle hole 5 in which the nozzles 4 are formed. Further, the initiator 20 is installed on the side opposite to the communicated portion of the combustion chamber 9 communicated with the through-hole 14 so that the ignition unit thereof is opposed to the communicated portion.

Figure 2:
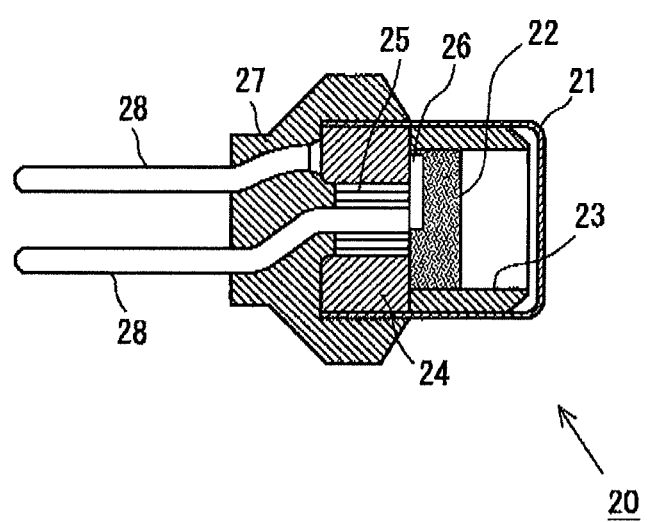
FIG. 2 shows a schematic arrangement of an initiator (ignition device) installed to the syringe shown in FIG. 1A.

An example of the initiator 20 will now be explained on the basis of FIG. 2. The initiator 20 is an electric ignition device. A space for arranging an ignition charge 22 is defined in a cup 21 by the cup 21 having a surface covered with an insulating cover. A metal header 24 is arranged in the space, and a cylindrical charge holder 23 is provided on an upper surface thereof. The ignition charge 22 is held by the charge holder 23. A bridge wire 26, which electrically connects one conductive pin 28 and the metal header 24, is wired at the bottom portion of the ignition charge 22. Two conductive pins 28 are fixed to the metal header 24 with an insulator 25 intervening therebetween so that they are in a mutually insulated state when no voltage is applied. Further, an opening of the cup 21, from which the two conductive pins 28 supported by the insulator 25 extend, is protected by a resin 27 in a state in which the insulation performance is maintained to be satisfactory between the two conductive pins 28.

In the initiator 20 constructed as described above, when the voltage is applied between the two conductive pins 28 by an external power source, then the current flows through the bridge wire 26, and the ignition charge 22 is combusted thereby. In this situation, the combustion product, which is produced by the combustion of the ignition charge 22, is spouted from the opening of the charge holder 23. Accordingly, in the present invention, the relative positional relationship of the initiator 20 with respect to the main syringe body 2 is designed so that the combustion product of the ignition charge 22, which is produced in the initiator 20, flows into the combustion chamber 9. Further, an initiator cap 12 is formed to have a brim-shaped cross section so that the initiator cap 12 is hooked by the outer surface of the initiator 20, and the initiator cap 12 is screw-fixed to the main syringe body 2. Accordingly, the initiator 20 is fixed to the main syringe body 2 by means of the initiator cap 12. Thus, the initiator 20 itself can be prevented from being disengaged from the main syringe body 2, which would be otherwise disengaged by the pressure brought about upon the ignition in the initiator 20.

The combination of the fuel component and the oxidizing agent component of the ignition charge 22 which is used for the syringe 1 is preferably exemplified by an explosive charge (ZPP) containing zirconium and potassium perchlorate, an explosive charge (THPP) containing titanium hydride and potassium perchlorate, an explosive charge (TiPP) containing titanium and potassium perchlorate, an explosive charge (APP) containing aluminum and potassium perchlorate, an explosive charge (ASO) containing aluminum and bismuth oxide, an explosive charge (AMO) containing aluminum and molybdenum oxide, an explosive charge (ACO) containing aluminum and copper oxide, and an explosive charge (AFO) containing aluminum and iron oxide, or an explosive charge composed of a combination of a plurality of the foregoing explosive charges. The explosive charges as described above exhibit such a characteristic that the plasma having a high temperature and a high pressure is generated during the combustion immediately after the ignition, but the generated pressure is suddenly lowered because no gas component is contained when the ordinary temperature is given and the combustion product is condensed.

Further, a cooling member 15, which is formed of a material made of metal as shown in FIGS. 1B(a) and 1B(b), is arranged along a side wall 9a of the combustion chamber 9 so that the central axis thereof in the extending direction is mutually overlapped with that of the combustion chamber 9. Specifically, the combustion chamber 9 is a space which has a volume of about 0.5 cc and which is formed to have a cylindrical shape. Therefore, the cooling member 15 is also formed to have a cylindrical shape in the same manner. A side surface 15a of the cooling member 15 shown in FIG. 1B(a) is formed such that a metal plate of aluminum, iron or the like, which is provided with a plurality of through-holes 15b, is curved to provide the cylindrical shape. The through-holes 15b are formed by means of any conventional technique including, for example, the punch press and the laser processing. On the other hand, the cooling member 15 shown in FIG. 1B(b) is formed such that a mesh plate made of metal (for example, metal lath, known wire mesh or the like), a metal plate having minute irregularities (projections and recesses) formed on the surface to increase the surface area or the like is curved to provide the cylindrical shape so that the cooling member 15 can be inserted into the combustion chamber 9. Therefore, the cooling member 15 shown in FIG. 1B(b) is formed with a large number of mesh holes 15c.

The cooling member 15, which is formed to have the cylindrical shape as shown in FIG. 1B, has openings which are formed at portions corresponding to a ceiling portion and a bottom portion in the axial direction. Accordingly, when the cooling member 15 is inserted into the combustion chamber 9, the combustion product, which is produced by the combustion of the ignition charge 22, easily flows into the combustion chamber 9. As a result, the combustion of a gas generating agent 30, which is to be started by the contact of the combustion product with the gas generating agent 30 as described later on, is hardly prevented from being started. It is also allowable that any structure or structural member is provided at the ceiling portion and/or the bottom portion of the cooling member 15 having the cylindrical shape, provided that the flow of the combustion product in the combustion chamber is unnecessarily intercepted or shut off.

Owing to the cooling member 15 which is constructed as described above and which is provided along the side wall 9a of the combustion chamber 9, the combustion product, which is produced from the ignition charge 22, is brought in contact with the cooling member 15. In this arrangement, the cooling member 15 is formed of the material made of metal, and hence the heat capacity thereof is relatively large. Therefore, the heat is deprived by the cooling member 15 from the combustion product brought in contact with the cooling member 15, and the temperature is immediately lowered to the ordinary temperature level. According to this fact, it is affirmed that the cooling member 15 exerts the cooling action on the combustion product. The combustion product, which is cooled to ordinary temperature by the cooling member 15 as described above, does not contain any component which behaves as the gas. Therefore, the pressure in the combustion chamber 9 can be lowered more effectively as compared with any situation in which the cooling member 15 is not provided. The characteristic of the pressure decrease is the characteristic which preferably contributes to the formation of the pressurizing mode for the injection solution in the syringe 1 according to the present invention. This feature will be described later on. It is noted that any explosive charge other than the above may be used as the ignition charge, provided that the pressurizing mode can be realized as described later on.

The cooling member 15, which has the through-holes 15b or the mesh holes 15c as shown in FIG. 1B, makes it possible to secure the wider contact area between the cooling member 15 and the combustion product allowed to flow thereinto. Therefore, the characteristic of the pressure decrease in the combustion chamber 9 as described above can be made more remarkable. The whole combustion product is not cooled to ordinary temperature by the cooling member 15. It is necessary that an amount of the combustion product, which has the heat required to start the combustion of the gas generating agent 30 as described later on, should be secured to reach the gas generating agent 30.

In this embodiment, a gas generating agent 30 having a columnar shape, which is combusted by the combustion product produced by the combustion of the ignition charge 22 to produce the gas, is arranged in the combustion chamber 9. The gas generating agent 30 is exemplified, for example, by a single base smokeless propellant composed of 98% by mass of nitrocellulose, 0.8% by mass of diphenylamine, and 1.2% by mass of potassium sulfate by way of example. It is also possible to use various gas generating agents used for a gas generator or an airbag and a gas generator for a seat belt pretensioner. Unlike the ignition charge 22 described above, in the case of the gas generating agent 30, the predetermined gas, which is produced during the combustion, contains the gas component even at the ordinary temperature. Therefore, the rate of decrease in the generated pressure is extremely small as compared with the ignition charge 22 described above. Further, the combustion completion time upon the combustion of the gas generating agent 30 is extremely long as compared with the ignition charge 22 described above. However, it is possible to change the combustion completion time of the gas generating agent 30 by adjusting the dimension, the size, and/or the shape, especially the surface shape of the gas generating agent 30 when the gas generating agent 30 is arranged in the combustion chamber 9. This is because the contact state, which is provided with respect to the combustion product of the ignition charge 22 allowed to flow into the combustion chamber 9, is considered to be changed depending on the surface shape of the gas generating agent 30 and the relative positional relationship between the gas generating agent 30 and the ignition charge 22 resulting from the arrangement of the gas generating agent 30 in the combustion chamber 9.

In the next place, a piston 6 made of metal is arranged in the through-hole 14 so that the piston 6 is slidable in the axial direction in the through-hole 14. One end thereof is exposed to the side of the combustion chamber 9, and a sealing member 7 is integrally attached to the other end. An injection solution ML, which is the injection objective substance to be injected from the syringe 1, is enclosed in a space formed in the through-hole 14 between the sealing member 7 and another sealing member 8. Therefore, the enclosing unit of the syringe, according to the present invention is formed by the sealing members 7, 8 and the through-hole 14. Each of the sealing members 7, 8 is made of rubber having the surface thinly coated with silicon oil so that the injection solution does not leak when the injection solution ML is enclosed, and the injection solution ML can be smoothly moved in the through-hole 14 in accordance with the sliding movement of the piston 6.

In this embodiment, a flow passage unit of the syringe 1 according to the present invention is formed on the forward end side of the syringe 1 (right side as viewed in FIG. 1A). Specifically, a holder 5, which is formed with nozzles 4 for allowing the injection solution ML to inject, is provided on the forward end side of the syringe 1. The holder 5 is fixed to the end surface of the main syringe body 2 with a gasket 3 intervening therebetween by the aid of a holder cap 13. The holder cap 13 is formed to have a brim-shaped cross section so that the holder cap 13 fixes the holder 5, and the holder cap 13 is screw-fixed to the main syringe body 2. Accordingly, the holder 5 is prevented from being disengaged from the main syringe body 2 by the pressure applied to the injection solution ML when the injection solution ML is allowed to inject.

A recess 10, which can accommodate the sealing member 8, is formed at a portion opposed to the sealing member 8 in a state in which the holder 5 is attached to the main syringe body 2. The recess 10 has approximately the same diameter as that of the sealing member 8, and the recess 10 has a depth which is slightly longer than the length of the sealing member 8. Accordingly, when the pressure is applied to the piston 6, and the injection solution ML is moved to the forward end side of the syringe 1 together with the sealing members 7, 8, then the sealing member 8 can be accommodated in the recess 10. When the sealing member 8 is accommodated in the recess 10, the pressurized injection solution ML is released. Thus, a flow passage 11 is formed at a portion of the holder 5 brought in contact with the side of the main syringe body 2 so that the released injection solution ML is guided to the nozzle 4. Accordingly, the released injection solution ML passes through the flow passage 11, and the injection solution ML is allowed to discharge from the nozzle 4 to the injection target. Owing to the fact that the recess 10 has the depth for accommodating the sealing member 8, any inhibition of the injection of the injection solution ML, which would be otherwise caused by the sealing member 8, can be avoided.

A plurality of nozzles 4 may be formed for the holder 5. Alternatively, one nozzle 4 may be formed. When the plurality of nozzles is formed, the flow passages, which correspond to the respective nozzles, are formed so that the released injection solution is fed to the respective nozzles. Further, when the plurality of nozzles 4 is formed, as shown in FIG. 1A(c), it is preferable that the respective nozzles are arranged at equal intervals around the central axis of the syringe 1. In this embodiment, the three nozzles 4, which are provided for the holder 5, are arranged at equal intervals around the central axis of the syringe 1. The diameter of the nozzle 4 is appropriately set while considering, for example, the injection target, the injection pressure applied to the injection solution ML, and the physical property (viscosity) of the injection solution.

In the syringe 1 constructed as described above, the combustion product or the predetermined gas is generated in the combustion chamber 9 by means of the ignition charge 22 provided in the initiator 20 and the gas generating agent 30 arranged in the combustion chamber 9 so that the pressure is applied to the injection solution ML enclosed in the through-hole 14 by the aid of the piston 6. As a result, the injection solution ML is pushed or extruded to the forward end side of the syringe 1 together with the sealing members 7, 8. When the sealing member 8 is accommodated in the recess 10, then the injection solution ML passes through the flow passage 11 and the nozzles 4, and the injection solution ML is allowed to inject to the injection target. The pressure is applied to the injection solution ML allowed to inject. Therefore, the injection solution ML penetrates through the surface of the injection target, and the injection solution ML arrives at the inside thereof. Accordingly, it is possible to achieve the purpose of the injection with the syringe 1.

Figure 3:
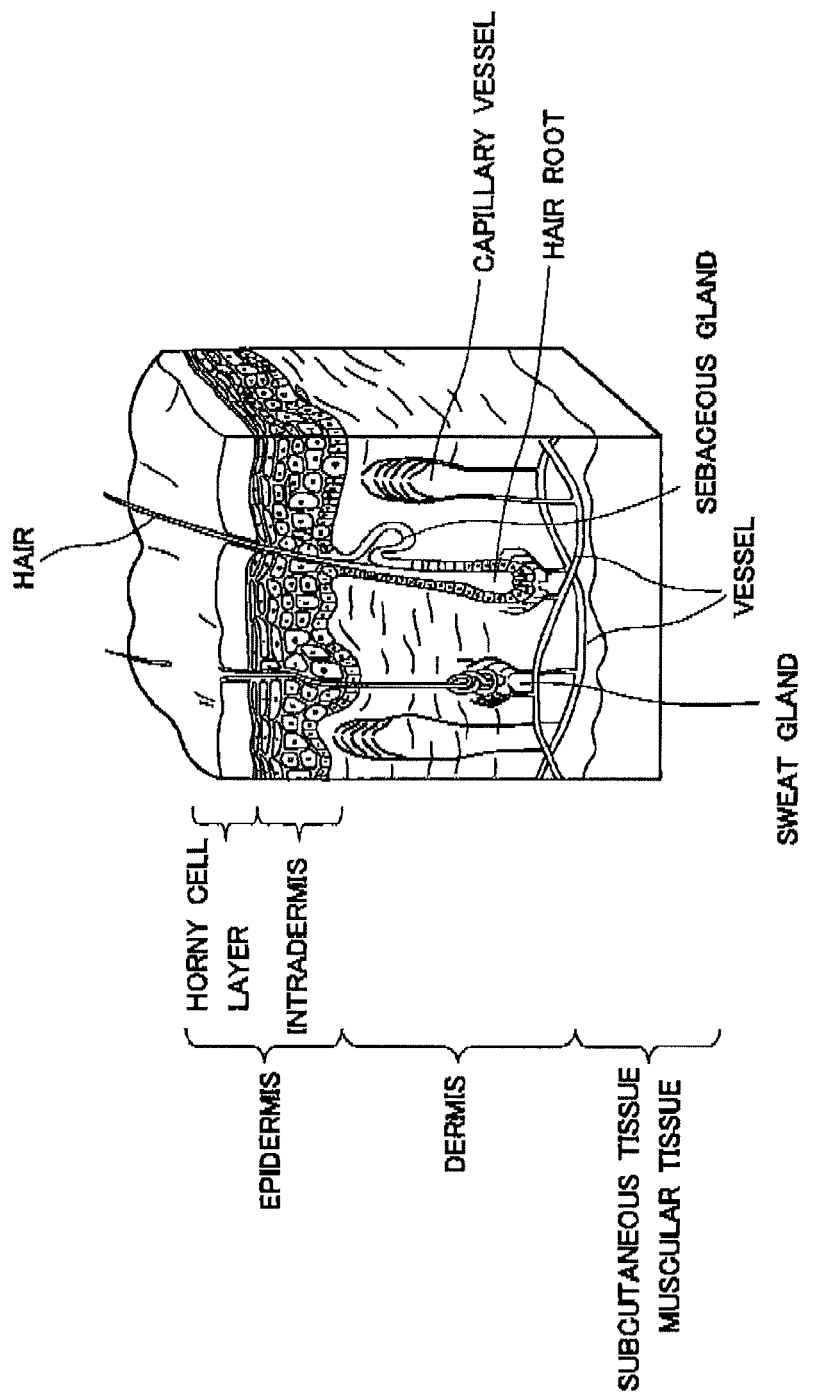
FIG. 3 schematically shows the skin structure of human.

In this embodiment, the injection target of the syringe 1 according to the present invention is the skin structure of the living body such as human, farm animal or the like. This specification principally refers to the action of the syringe 1 exerted on the human skin. Therefore, FIG. 3 schematically shows an anatomical structure of the human skin. The human skin is constructed in a layered form including epidermis, dermis, subcutaneous tissue (hypodermis), and muscular tissue as disposed in the depth direction from the side of the skin surface. Further, the epidermis can be distinguished or classified into horny cell layer and intradermis in a layered form. In each of the layers of the skin structure, the tissue and the main cells or the like for constructing the tissue have different features as well.

Specifically, the horny cell layer is principally composed of keratinocytes, and the horny cell layer is positioned on the outermost surface side of the skin. Therefore, the horny cell layer has the function of the so-called barrier layer. In general, the thickness of the horny cell layer is about 0.01 to 0.015 mm, and the horny cell layer performs the surface protection for human by keratinocytes. Therefore, in order to physically insulate the interior of the human body from the external environment to some extent, a relatively high strength is required as well. On the other hand, the intradermis is constructed to include dendritic cells (Langerhans cells) and pigment cells (melanocytes). The epidermis is formed by the horny cell layer and the intradermis. The thickness of the epidermis is generally about 0.1 to 2 mm. It is considered that the dendritic cells in the intradermis are cells which participate in the antigen-antibody reaction. This is because the dendritic cells recognize the presence of the antigen by incorporating the antigen, and the antigen-antibody reaction, in which lymphocytes are activated to play a role to attach the foreign matter, tends to be induced. On the other hand, the pigment cells in the intradermis have the function to avoid the influence of the ultraviolet light radiated from the external environment.

In the next place, vessels and capillary vessels on the skin are complicatedly spread all over the dermis. Further, for example, sweat glands for adjusting the body temperature, hair roots of body hair (including hair on the head), and sebaceous glands associated therewith also exist in the dermis. The dermis is the layer which makes communication between the epidermis and the interior of the human body (subcutaneous tissue and muscular tissue). The dermis is constructed to include fibroblasts and collagen cells. Therefore, the state of the dermis greatly participates, for example, in the hair falling out and the appearance of wrinkles due to the so-called collagen shortage or the elastin shortage.

In this way, the skin structure of human is generally formed in the layered form. The intrinsic anatomical function is exhibited, for example, by the cells and the tissue principally contained in each of the layers. This means the fact that it is desirable to inject a component (ingredient) for a medical treatment to a place (depth) of the skin structure in conformity with the purpose of the medical treatment, for example, when the medical treatment is applied to the skin. For example, the dendritic cells exist in the intradermis. Therefore, when a vaccine injection is performed therein, it is possible to expect a more effective antigen-antibody reaction. However, in the case of the conventional injection technique, it is difficult to perform the vaccine injection with respect to the intradermis'which is positioned at the relatively shallow portion. Even when such a vaccine injection is performed, the injection greatly depends on the skill of a health care worker or medical professional. Further, the pigment cells exist in the intradermis, and hence it is also demanded that when a beauty treatment is performed for the so-called skin whitening, a specified component (ingredient) for the skin whitening is injected into the intradermis. However, in the case of the conventional technique, it is difficult to perform such a treatment as described above.

In the next place, fibroblasts and collagen cells exist in the dermis. Therefore, for example, if protein for removing skin wrinkles, enzyme, vitamin, amino acid, mineral, sugar, nucleic acid, and various growth factors (epithelial cells and fibroblasts) are injected into the dermis, an effective beauty treatment effect is expected. However, the dermis is also positioned at the relatively shallow portion in the same manner as the intradermis. Therefore, in the case of the conventional technique, it is difficult to perform the beauty treatment by means of the injection in many cases. As for a hair regeneration treatment, the hair roots are positioned in the dermis. Therefore, in order to perform the hair regeneration treatment, the following procedure is considered to be favorable. That is, for example, a stem cell injection method, in which dermal papilla cells and/or epidermal stem cells are autologous cultured and cultured cells are autologous transplanted to the scalp, is performed, or several types of growth factors and/or nutrient components extracted from stem cells are injected into a portion positioned in the vicinity of the dermis.

In this way, the substance, which is injected in accordance with the purpose of the treatment for the skin, individually corresponds to the position (depth) in the skin structure into which the substance is desirably injected. However, it is difficult for the conventional technique to adjust the injection position. In the case of the syringe 1 according to the present invention, the depth, at which the injection solution arrives in the skin structure, can be preferably adjusted by adjusting the pressure applied to the injection solution. As described above, various substances (injection objective substances) are used to be injected into the skin structure depending on the purpose of the treatment thereof. Therefore, the injection objective substance is generally referred to as "injection solution" in the following description. However, this includes no intention to limit the form and the contents of the substance to be injected. As for the injection objective substance, the component (ingredient), which is to be delivered to the skin structure, may be either dissolved or not dissolved. Any specified form is also available for the injection objective substance provided that the injection objective substance can be allowed to inject to the skin structure from the nozzle 4 by being pressurized. It is possible to adopt various forms including, for example, liquid and gel forms.

For example, the injection objective substance usable in the beauty treatment is exemplified, for example, by protein for skin whitening or for removing wrinkles, enzyme, vitamin, amino acid, mineral, sugar, nucleic acid, and various growth factors (epithelial cells and fibroblasts). Further, the injection objective substance in the hair regeneration treatment is exemplified, for example, by dermal papilla cell, hair root stem cell, epidermal stem cell, HARG cocktail, and hair for transplantation.

Figure 4:
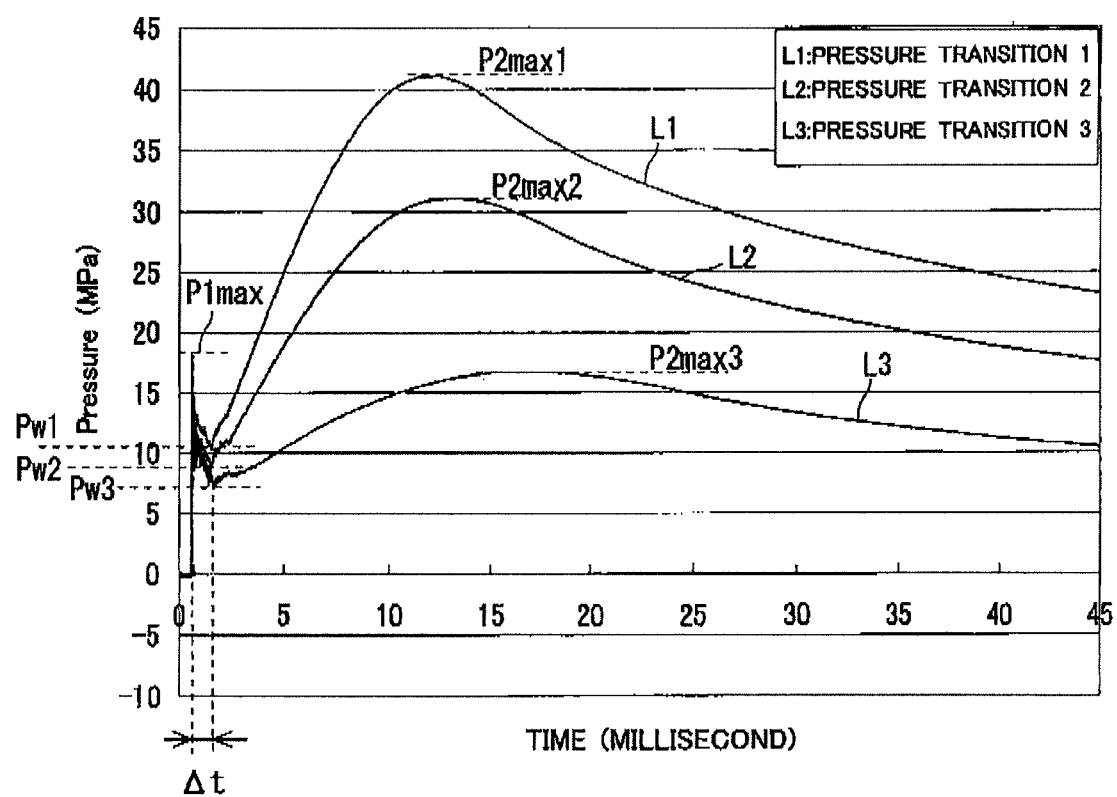
FIG. 4 shows the transition of the pressure applied to the injection solution in the syringe shown in FIG. 1A.

In the next place, an explanation will be made on the basis of FIG. 4 about the specified pressurizing form for the injection solution as performed in the syringe 1. FIG. 4 shows the pressure transition applied to the injection solution enclosed in the through-hole 14 by the aid of the piston 6 by appropriately adjusting the combination of the ignition charge 22 and the gas generating agent 30 contained in the syringe 1. The horizontal axis of FIG. 4 represents the elapsed time in millisecond, and the vertical axis represents the applied pressure in MPa. The pressure can be measured by installing a pressure gauge in a pressure measuring port (not shown in FIG. 1) provided to make communication with the combustion chamber 9 in the main syringe body 2. In the example shown in FIG. 4, the pressure transitions, which are provided when three types of amounts of the gas generating agent 30 are combined with the same amount of ZPP (containing zirconium and potassium perchlorate) as the ignition charge 22, are shown as L1, L2, L3 in FIG. 4.

An explanation will now be made about the pressure transitions L1 to L3 in the syringe 1 according to the present invention. The pressure transitions involve the common technical feature. At first, the common technical feature will be explained on the basis of the pressure transition L2. In the pressure transition in the present invention, the combustion of the ignition charge 22 is started immediately after the application of the electricity to the initiator 20, and thus the pressure suddenly arrives at the first peak pressure value P1max from the state in which the pressure is zero. After that, the pressure is lowered to the waiting pressure Pw2 (the waiting pressure is represented by Pw1 in the pressure transition L1, and the waiting pressure is represented by the waiting pressure Pw3 in the pressure transition L3). The process, in which the pressure is applied to the injection solution in accordance with the pressure transition as provided until arrival at this point, is referred to as "first pressurizing mode". After that, the pressure is raised again, and the pressure arrives at the second peak pressure P2max2 (the second peak pressure is represented by P2max1 in the pressure transition L1, and the second peak pressure is represented by P2max3 in the pressure transition L3). After that, the pressure is gently lowered. The process or step, in which the pressure is applied to the injection solution in accordance with the pressure transition for raising the pressure from the waiting pressure to the second peak pressure, is referred to as "second pressurizing mode". In this way, each of the pressure transitions L1 to L3 is constructed by the first pressurizing mode and the second pressurizing mode.

The two different pressurizing modes, which are provided in one pressure transition as described above, are realized by the ignition charge 22 and the gas generating agent 30 which have the different combustion modes or forms. That is, the feature of the combustion form of the ignition charge 22 resides in the instantaneous combustion brought about by the application of the electricity to the initiator 20. Further, when the produced combustion gas is condensed at the ordinary temperature, no gas component is contained therein, as represented by ZPP. Therefore, the pressure, which is applied to the injection solution, is suddenly lowered. In particular, the cooling member 15 is provided in the combustion chamber 9 as described above. Therefore, the decrease in the temperature of the combustion product can be effectively caused, and thus the decrease in the pressure applied to the injection solution can be made steeper. Therefore, the pressure transition, which is based on the first pressurizing mode, is completed in a minute time Δt shown in FIG. 4. On the other hand, the combustion product, which is produced by the combustion of the ignition charge 22, flows into the combustion chamber 9, and the gas generating agent 30 arranged therein is combusted thereby. Accordingly, the combustion of the gas generating agent 30 is started. Therefore, the gas generating agent 30 is combusted during the pressure transition based on the first pressurizing mode or immediately after the completion of the first pressurizing mode, and the predetermined gas is produced thereby. The velocity of the generation of the gas from the gas generating agent 30 is extremely gentle as compared with the velocity of the generation of the combustion product from the ignition charge 22. In other words, the combustion completion time of the gas generating agent 30 is longer than the combustion completion time of the ignition charge 22. Therefore, as clarified from FIG. 4 as well, the pressure transition is depicted such that the pressure increase rate, which is provided from the waiting pressure Pw2 until arrival at the second peak pressure P2max2, is gentler than the pressure increase rate which is provided upon the ignition of the ignition charge 22. This feature is provided in the same manner for the pressure transitions L1, L3 as well.

Figure 5:
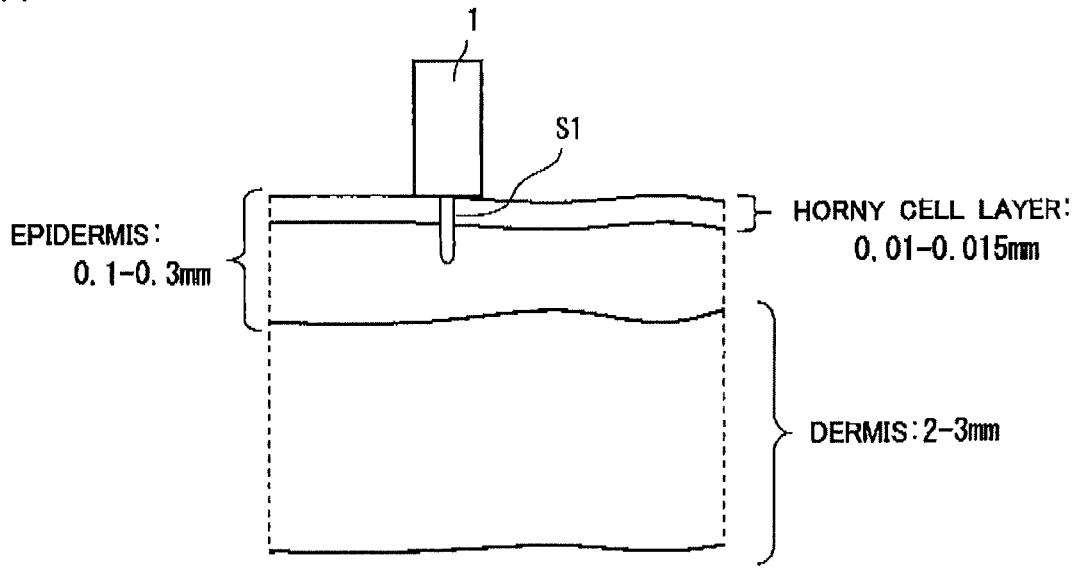
FIG. 5 shows a situation in which the injection solution is diffused in the skin structure of human when the pressure, which is in the transition as shown in FIG. 4, is applied to the injection solution.
Figure 5:
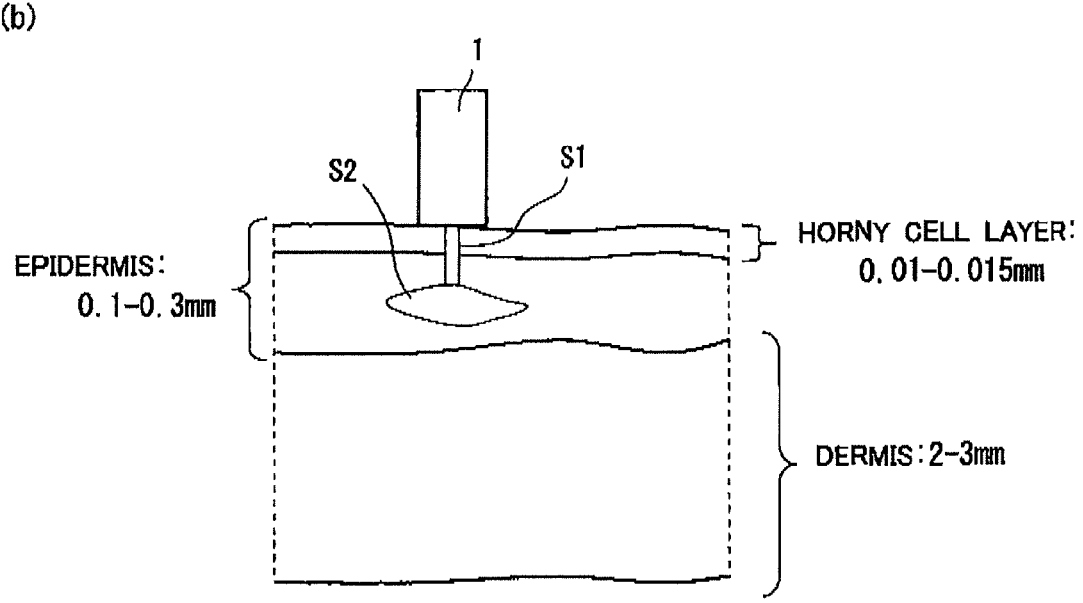

An explanation will be made on the basis of FIG. 5 about the conceptual injection situation of the injection solution in the human skin structure in accordance with the pressure transition based on the two pressurizing modes as described above. In the first pressurizing mode performed in the minute time Δt (time ranging from the application of electricity in the initiator 20 to the arrival at the waiting pressure Pw2), as shown in FIG. 5(*a*), a minute amount of the injection solution is allowed to inject from the syringe 1. In the injection of the minute amount of the injection solution, the energy amount, which is possessed by the injection solution allowed to inject depending on the injection amount per unit time, i.e., the injection flow rate, is determined by Expression 1 as follows.

$$P = \tfrac{1}{8} \cdot \pi \rho D^2 u^3 \qquad \text{(Expression 1)}$$

P: energy of discharging injection solution, ρ: density of injection solution, D: diameter of nozzle 4, u: discharging velocity of injection solution.

It is noted that Expression 1 merely calculates the energy amount possessed by the injection solution allowed to inject. Even when only Expression 1 is provided, it is insufficient to explain the adjustment of the injection depth in the skin structure. That is, in order to adjust the injection depth, it is necessary to perform the pressure control according to the present invention. In view of the above, an explanation will be made below about the pressure control according to the present invention in relation to the adjustment of the injection depth in the skin structure while taking Expression 1 into consideration.

In the first pressurizing mode, the pressure transition, in which the pressure arrives at the waiting pressure via the peak pressure P1max from zero, is performed in the extremely short period of time. Therefore, it is also affirmed that the injection solution having the high energy is allowed to inject to the skin in this process. As a result, the injection solution, which is allowed to inject in the first pressurizing mode, penetrates through the outermost surface of the skin, and the injection solution erodes the inside of the skin (discharging injection solution is represented by S1 in FIG. 5(*a*)). In this situation, it is considered that the injection depth is more deepened as the energy of the discharging injection solution in the first pressurizing mode represented by Expression 1 is more increased. In this context, according to Expression 1, the energy P of the discharging injection solution is proportional to the product of the cube of the discharging velocity u of the injection solution and the density of the injection solution. Therefore, the larger the peak pressure P1max is, the larger the energy P of the discharging injection solution is. Further, the shorter the minute time Δt for the execution of the first pressurizing mode is, the smaller the energy P is. Therefore, the injection depth, at which the injection solution can arrive in the skin, can be adjusted by adjusting the energy P. FIG. 5(*a*) schematically shows the situation in which the injection solution arrives at the layer portion of the epidermis in the human skin structure. However, when the energy amount is adjusted, then the injection depth can be made deeper in the first pressurizing mode, or the injection depth can be made shallower. In particular, the cooling member 15 is provided in the combustion chamber 9. Therefore, it is possible to effectively shorten the time Δt ranging from the state in which the pressure is zero to the waiting pressure via the peak pressure P1max. Therefore, it is considered that the cooling member 15 greatly contributes to the achievement of the shallower injection depth in the first pressurizing mode.

In this context, the waiting pressure, at which the pressure arrives in the first pressurizing mode, is such a pressure that the erosion, which is caused by the discharging injection solution in the first pressurizing mode in the injection depth direction at the inside of the skin structure, is mitigated, and the diameter of the penetrating passage can be reduced or shrunk at a part of the penetrating passage for the injection solution formed in the skin structure. In this case, when the pressure is raised to the peak pressure P1max and the pressure is thereafter lowered to the waiting pressure, then the energy amount possessed by the injection solution is lowered. Therefore, the erosion of the skin caused by the injection solution is mitigated, and the discharging injection solution does not arrive at the deepest portion of the skin structure. Further, the skin structure of the living body has a certain elastic force. Therefore, on account of the elastic force, the diameter of the penetrating passage may be reduced or contracted by the elastic force while including the injection solution or scarcely including the injection solution at a part of the penetrating passage having been already formed, especially on the forward end side (deep side in the depth direction). As a result, the state, in which the diameter is reduced, is formed on the forward end side of the penetrating passage, and the state, in which the diameter is not reduced, is maintained on the proximal end side of the penetrating passage, at the point in time at which the pressure arrives at the waiting pressure in the first pressurizing mode. Therefore, the difference in strength with respect to the pressure of the injection solution is generated between the forward end side and the proximal end side of the penetrating passage. That is, the strength is relatively high on the forward end side of the penetrating passage as compared with the proximal end side thereof. As a result, when the pressurization is performed again in the second pressurizing mode as described later on, then the pressure of the injection solution is uniformly applied to the entire penetrating passage, but the penetrating passage portion, which is in the unreduced diameter state, has the strength weaker than that of the reduced diameter portion, because the penetrating passage portion in the unreduced diameter state is relatively enlarged or expanded. It is considered that this situation contributes to the diffusion of the injection solution. According to the above, it is desirable that the waiting pressure is the pressure which is lowered from the peak pressure P1max in the first pressurizing mode to such an extent that the forward end side of the penetrating passage is contracted or shrunk by the elastic force exerted from the skin structure in the second pressurizing mode as described later on, i.e., to such an extent that the difference in strength of the penetrating passage, which can secure or guarantee the diffusion of the injection solution in accordance with the second pressurizing mode, is generated. For example, it is preferable that the waiting pressure is not more than 50% of the peak pressure P1max.

In the next place, the pressure transition, in which the pressure is raised from the waiting pressure Pw2 to the second peak pressure P2max2, is depicted in the second pressurizing mode. When the pressure of the injection solution is raised again in accordance with the second pressurizing mode from the state in which it is estimated that the difference in strength is generated in the penetrating passage formed by the injection solution owing to the arrival of the pressure of the injection solution at the waiting pressure Pw2 in accordance with the first pressurizing mode, it is considered that the injection solution, which is confined in the penetrating passage having the reduced diameter, is pressurized again. However, the injection solution, which is allowed to inject in the second pressurizing mode, behaves to pressurize the skin structure by the aid of the injection solution existing at the unreduced diameter portion rather than to directly act on the bottom of the penetrating passage, on account of the difference in strength as described above. Therefore, the injection solution causes the permeation into the interior of the skin structure from the penetrating passage in the unreduced diameter state, rather than the further erosion in the depth direction. In other words, it is considered that the injection solution is diffused to the interior of the tissue of the skin structure via the portion of the penetrating passage in the unreduced diameter state which is considered to have the relatively low strength with respect to the pressure (in FIG. 5(b), the injection solution, which is diffused in accordance with the second pressurizing mode, is represented by S2). Further, the pressure increase rate, which is provided in the second pressurizing mode, is gentler than the pressure increase rate which is provided in the first pressurizing mode. Therefore, the injection solution can be diffused into the skin along the extending direction of the layered tissue of the skin structure without uselessly deepening the injection depth of the injection solution. FIG. 5(b) shows the diffusion state as described above merely conceptually. When the injection depth is set to any different depth as viewed in FIG. 5(a), the diffusion state differs as well. For example, it is also possible to effect the diffusion so that the injection solution is permeated into a portion disposed nearer to the dermis or into the dermis.

The period of time, in which the second pressurizing mode is continued, is determined depending on the amount of the injection solution (injection amount) allowed to inject by the syringe 1. After the passage of the second peak pressure P2max2, the pressure, which is applied to the injection solution, is gradually lowered. However, the pressure becomes zero at the point in time at which the injection solution allowed to inject from the nozzles 4 is exhausted, and the second pressurizing mode comes to the end. The purpose of the second pressurizing mode is to diffuse the injection solution to the desired depth of the skin structure. Therefore, it is preferable that the injection solution amount, which is allowed to inject from the syringe 1 in the second pressurizing mode, is larger than the injection solution amount which is allowed to inject in the first pressurizing mode. This situation can be sufficiently realized, because the first pressurizing mode is performed within the minute time Δt as described above.

In this way, in the case of the syringe 1 according to the present invention, the pressure transition advances such that the pressure undergoes the waiting pressure in the first pressurizing mode and the injection solution is diffused in accordance with the second pressurizing mode. Accordingly, the injection solution can be fed to the desired depth in the skin structure. In particular, in the first pressurizing mode, the period of time, which elapses until the pressure arrives at the waiting pressure, can be further shortened owing to the presence of the cooling member 15. Therefore, the diffusion preparatory state, which is the state to diffuse the injection solution, can be formed at the shallower portion of the skin structure. Further, the pressurization, which is performed in the second pressurizing mode, is principally directed to the diffusion of the injection solution, and the injection depth is prevented from being uselessly deepened. Therefore, it is possible to precisely diffuse the injection solution even at such a portion that the injection depth is relatively shallow.

An explanation will now be made about the pressure transitions L1, L2, L3 shown in FIG. 4 respectively. In these pressure transitions, the peak pressures, which are provided in the first pressurizing mode, are approximately P1max and coincident with each other by utilizing the same initiator 20. The waiting pressures are dispersed in a range of Pw1 to Pw3. However, as described above, as for the waiting pressure, when the pressure is lowered to some extent from the peak pressure in the first pressurizing mode, then the erosion caused by the discharging injection solution in the first pressurizing mode, which occurs in the injection depth direction at the inside of the skin structure, is mitigated, and the pressure may behave such a pressure that the diameter of the penetrating passage can be contracted or reduced at the part of the penetrating passage for the injection solution provided in the skin structure. In this way, even when the same initiator 20 is used, the gas generating agents 30, each of which is arranged in the combustion chamber 9, have the different amounts. Accordingly, the pressure transitions in the second pressurizing mode are changed as shown in FIG. 4. Specifically, in the case of the pressure transition L1, the amount of the gas generating agent 30 is maximized. In the case of the pressure transition L3, the amount of the gas generating agent 30 is minimized. In the case of the pressure transition L2, the amount of the gas generating agent 30 is the intermediate amount. Therefore, the peak pressures in the second pressurizing mode reside in a relationship of P2max1 in pressure transition L1>P2max2 in pressure transition L2>P2max3 in pressure transition L3. According to the three types of the pressure transitions as described above, it is possible to provide the different speeds to diffuse the injection solution and the different amounts of the injection solution to be diffused at approximately the same injection depth.

The peak pressure P2max3, which is provided in the pressure transition L3, has the value which is lower than that of the peak pressure P1max provided in the first pressurizing mode. In this procedure, the pressure difference between P1max and P2max3 is within a predetermined ratio with respect to P1max. This is because it is intended to clarify the pressure transition in which the injection solution is diffused in accordance with the second pressurizing mode after undergoing the waiting pressure in the first pressurizing mode, unlike any pressure transition based on the conventional technique, in order to feed the injection solution to the desired depth in the skin structure. The predetermined ratio is exemplified by 60% of P1max.

The peak pressures P2max1, P2max2, which are provided in the second pressurizing mode in the pressure transitions L1, L2, have the values which exceed the peak pressure P1max provided in the first pressurizing mode. The peak pressures P2max1, P2max2 as described above are appropriately set in order to realize the desired injection amounts.

The foregoing embodiment is explained assuming that the human skin structure is used. However, the syringe according to the present invention can be used as the syringe for animals (for example, farm animal, pet or the like) other than human. In this case, the type and the amount of the ignition charge 22 carried on the initiator 20 and the type and the amount of the gas generating agent 30 are appropriately adjusted while considering the characteristic of the skin structure of the injection target, for example, the Young's modulus or the like.

In the foregoing embodiment, the pressure is applied to the injection objective substance in the syringe 1. However, it is also allowable that the injection objective substance is, for example, a powder or a granular solid, provided that the injection objective substance can be allowed to inject from the syringe 1.

EXAMPLES

Experimental conditions and experimental results will now be described below in relation to injection experiments (Experiments 1 to 4) performed by using the syringe 1 according to the present invention. The following experimental conditions were set in order to diffuse the injection solution intensively or in a concentrated manner into the skin layer of a pig as an injection target.

<Experimental Conditions>
(About Syringe 1)

87 mg of ZPP (zirconium and potassium perchlorate) mixture was used for the ignition charge 22 of the initiator 20, and single base propellant in an amount shown in Table 1 below was used for the gas generating agent 30. The diameter of the nozzle 4 is 0.1 mm, and the three nozzles 4 are arranged concentrically.

The component ratio of the single base propellant is as follows.

Nitrocellulose: 98.1% by weight;
Diphenylamine: 0.8% by weight;
Potassium sulfate: 1.1% by weight;
Graphite (loss ratio (outage)): minute amount.

(About Injection Target)

In this embodiment, a skin portion of abdomen of a pig was used as the injection target. Specifically, the pig was sacrificed, and then the skin portion was peeled off, followed by being stored for 6 days in a physiological saline solution at 9° C. to prepare a sample (cooled and stored), or followed by being frozen and stored at −70° C. and thawed thereafter to prepare a sample.

(About Injection Solution)

In order to easily grasp the diffusion situation of the injection solution after the injection, a colored aqueous solution (methylene blue) was used.

TABLE 1

|  | Experiment 1 | Experiment 2 | Experiment 3 | Experiment 4 |
| --- | --- | --- | --- | --- |
| Initiator | ZPP | ZPP | ZPP | ZPP |
| Amount of ignition charge | 87 mg | 87 mg | 87 mg | 87 mg |
| Amount of gas generating agent | Single base propellant 150 mg | Single base propellant 90 mg | Single base propellant 180 mg | Single base propellant 150 mg |
| Injection target | Frozen pig | Cooled pig | Cooled pig | Cooled pig |

<Experimental Results>

Figure 6A:
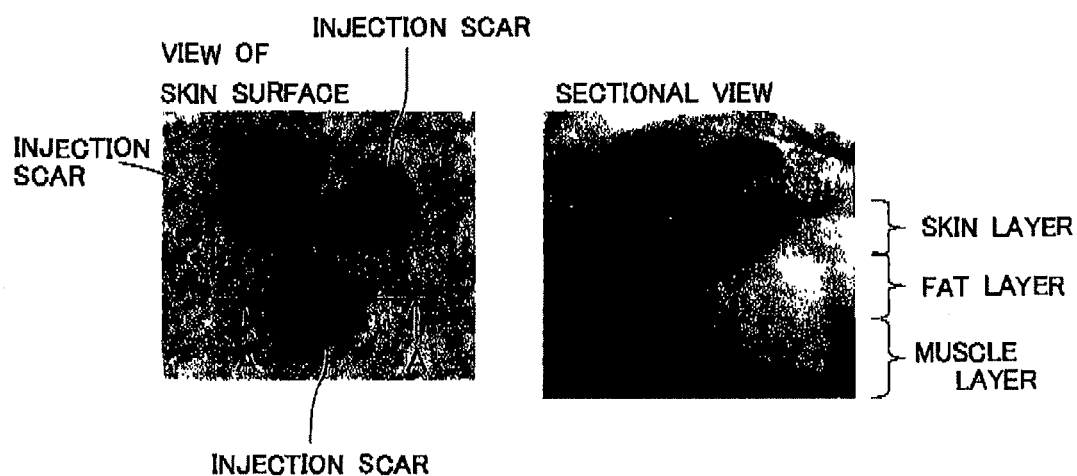
FIG. 6A shows a first view illustrating a result of an injection experiment by using the syringe according to the Present invention.
Figure 6B:
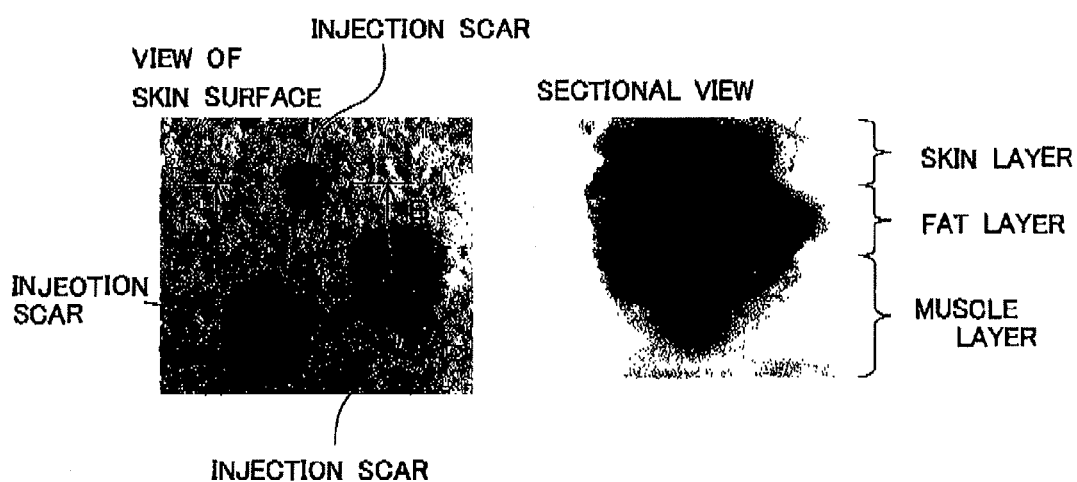
FIG. 6B shows a second view illustrating a result of an injection experiment by using the syringe according to the present invention.
Figure 6C:
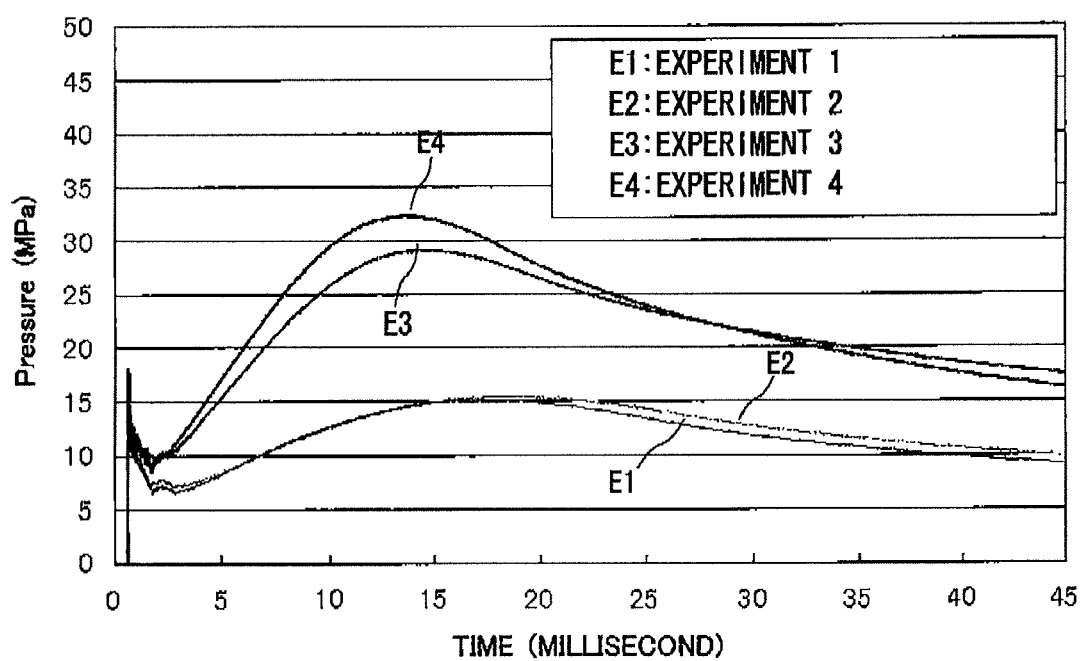
FIG. 6C shows a third view illustrating a result of an injection experiment by using the syringe according to the present invention.

Next, the experimental results as obtained in accordance with the foregoing experimental conditions are shown below. FIG. 6A shows a view illustrating a pig skin surface in relation to an injection result in Experiment 3 and a sectional view thereof (cross section taken along AA). On the other hand, FIG. 6B shows a view illustrating a pig skin surface in relation to an injection result in Experiment 4 and a sectional view thereof (cross section taken along BB). Further, FIG. 6C shows graphs illustrating the pressure transitions applied to the injection solution in Experiment 1 to Experiment 4 respectively. Table 2 shown below summarizes the predetermined pressure values in the pressure transitions and the times required to arrive at the pressures respectively. The pressure, which was applied to the injection solution, was measured by using an electrostrictive element (piezoelectric element) at a detection frequency of 100,000 times per second, i.e., every 0.01 millisecond. The maximum pressure, which was detected immediately after the operation of the initiator 20, was adopted for the first peak pressure shown in Table 2 below. An average value of the data was adopted for the waiting pressure, the data including the data as obtained within 0.05 ms before and after the minimum pressure (i.e., pieces of data obtained at respective five points provided therebefore and thereafter) recorded in such an interval that the pressure was lowered from the first peak pressure during the period in which the gas generating agent 30 was completely ignited after the operation of the initiator 20. The maximum pressure, which appeared after the arrival at the waiting pressure, was adopted for the second peak pressure. The respective times required to arrive shown in Table 2 mean the periods of time required until arrival at the respective pressures by using, as the start point, the point in time at which the ignition current was allowed to flow to the initiator 20.

TABLE 2

|  | Exp. 1 | Exp. 2 | Exp. 3 | Exp. 4 |
| --- | --- | --- | --- | --- |
| First peak pressure (MPa) | 16.8 | 17.5 | 18.0 | 17.4 |
| Time required to arrive at first peak pressure (ms) | 0.61 | 0.60 | 0.61 | 0.61 |
| Waiting pressure (MPa) | 6.73 | 7.39 | 8.95 | 6.84 |
| Time required to arrive at waiting pressure (ms) | 1.73 | 1.74 | 1.71 | 1.74 |
| Second peak pressure (MPa) | 15.1 | 15.4 | 32.3 | 29.2 |
| Time required to arrive at second peak pressure (ms) | 17.29 | 18.19 | 13.61 | 14.60 |
| Waiting pressure ratio (waiting pressure/first peak pressure) | 0.40 | 0.42 | 0.50 | 0.51 |

The foregoing experimental results are analyzed as follows. That is, in Experiments 1, 2, and 3, the injection solution, which was allowed to inject from all of the three nozzles 4 provided for the syringe 1, was successfully diffused at the desired injection depth in the skin layer of the pig. For example, as shown in FIG. 6A corresponding to Experiment 3, as overlooked from the skin surface, it is appreciated that the injection scars are spread in approximately identical sizes at three positions. In the cross section, the injection solution is not uselessly spread to the fat layer and the muscle layer, and the injection solution is diffused in a state of staying in the skin layer. If the injection solution is vaccine, the vaccine can be fed and diffused intensively or in a concentrated manner to the area in which it can be expected to cause the effective antigen-antibody reaction. Also in Experiments 1 and 2 which are not shown, the effective diffusion of the injection solution was successfully confirmed in the same manner as in Experiment 3 shown in FIG. 6A.

On the other hand, in Experiment 4, as for the injection solution allowed to inject from one nozzle of the three nozzles 4, the injection solution is somewhat spread to the fat layer and the muscle layer unlike Experiments 1 to 3 (see a sectional view shown in FIG. 6B corresponding to Experiment 4). Further, as overlooked from the skin surface shown in FIG. 6B, it is acknowledged that the size of the injection scar corresponding to the sectional view is smaller than those of the injection scars formed at the other two positions. This is because the injection solution arrived at the deeper position of the injection target as shown in the sectional view in relation to the small injection scar, and the amount of the injection solution, which was successfully confirmed from the surface, was decreased. However, although not shown, the effective diffusion of the injection solution was successfully confirmed for the two nozzles other than the nozzle shown in FIG. 6B in the same manner as in Experiments 1 to 3.

Based on the foregoing fact, it is affirmed that when the waiting pressure ratio (defined as the value obtained by dividing the waiting pressure by the first peak pressure) has the value lower than the predetermined value, the injection solution, which is allowed to inject from at least any one of the nozzles 4, can be effectively diffused into the skin layer of the pig, wherein it is possible to find out the significance of practical use. More preferably, when the waiting pressure ratio is not more than 0.50, it is considered that the effective diffusion is realized for the injection solution allowed to inject from all of the three nozzles 4 as shown in Experiments 1 to 3. In the case of any conventional needle-free syringe, the injection solution has been fed to the deep inside of the injection target to such an extent that the injection scar cannot be confirmed even by being overlooked from the skin surface unlike the present invention. Taking this fact into consideration, it is affirmed that the syringe 1 according to the present invention provides the useful effect which can be never realized by the conventional needle-free syringe.

<Another Embodiment Concerning Cooling Structure for Combustion Product>

Figure 7:
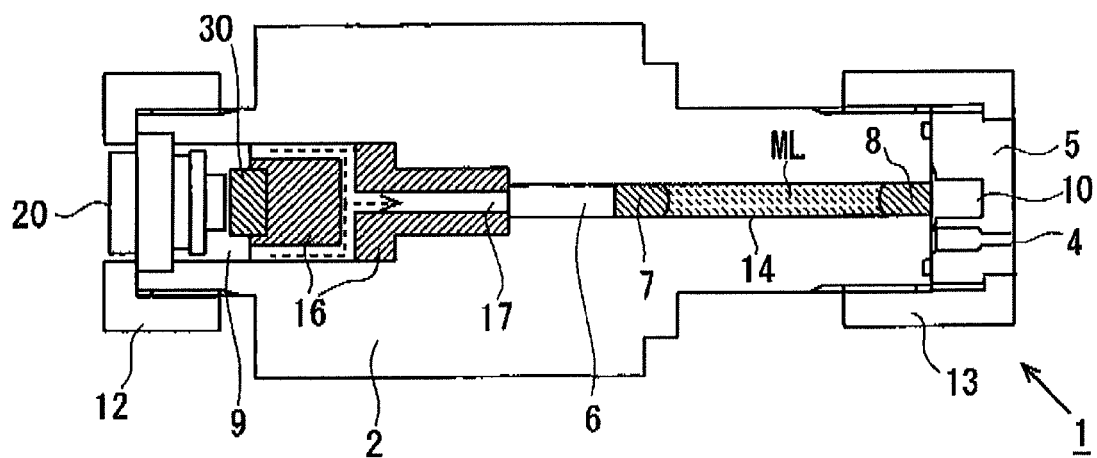
FIG. 7 shows another schematic arrangement of a syringe according to the present invention.
Figure 7:
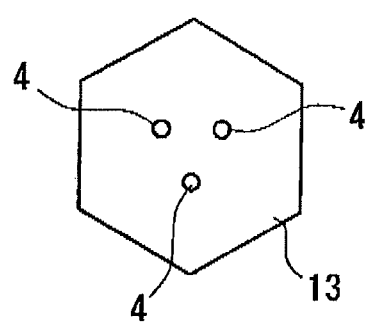

FIG. 7 shows a schematic arrangement of another cooling structure for the combustion product produced from the ignition charge 22, as adoptable for the syringe 1 according to the present invention. FIG. 7(*a*) shows a sectional view illustrating a syringe 1, and FIG. 7(*b*) shows a side view as viewed from the side of the nozzles 4. Substantially the same constitutive parts or components, which are provided in the arrangement of the syringe 1 shown in FIG. 1 and the arrangement of the syringe 1 shown in FIG. 7, are designated by the same reference numerals, and thus any explanation thereof will be omitted. In the syringe 1 shown in FIG. 7, the volume of the combustion chamber 9 is larger than the volume of the combustion chamber of the syringe shown in FIG. 1, and the syringe 1 shown in FIG. 7 has the volume of about 2 cc which is about four times the volume of the combustion chamber of the syringe shown in FIG. 1. A metal member 16, which has an integrated block-shaped form, is arranged in the combustion chamber 9 adjacently to the piston 6 to such an extent that the metal member 16 is brought in contact with an end portion of the piston 6. A through-hole 17, which is open at an end surface opposed to the initiator 20, which is also open at an end surface brought in contact with the piston 6, and which makes communication between the both openings, is formed at the inside of the metal member 16. That is, the through-hole 17 is a space which connects the piston 6 and a residual space in the combustion chamber 9 in which the metal block 16 is arranged. Therefore, the pressure, which is generated in the combustion chamber 9, for example, by the combustion product of the ignition charge, is transmitted to the piston 6 via the through-hole 17 in this structure (transmission of pressure is indicated by dotted arrow in FIG. 7(*a*)).

Further, the gas generating agent 30 is arranged at an end portion of the metal member 16 disposed on the side of the initiator 20. Therefore, at least a part of the combustion product, which is produced from the ignition charge 22, can reach the gas generating agent 30 in the combustion chamber 9 without being intercepted or shut off by the metal member 16. Accordingly, the pressurization, which is effected in accordance with the second pressurizing mode as described above, is also performed without causing any problem.

In the syringe 1 constructed as described above, the metal member 16, which has the relatively large volume, is arranged in the combustion chamber 9. Accordingly, the volume of the combustion chamber is decreased, and it is possible to more effectively deprive the heat from the combustion product produced from the ignition charge 22. Further, the pressure in the combustion chamber can be instantaneously raised by the combustion product. That is, the combustion chamber 9 is widened as compared with the syringe 1 shown in FIG. 1, and the metal member 16 is arranged therein. Accordingly, the time Δt, which elapses from the state in which the pressure is zero to the waiting pressure via the peak pressure P1max in the first pressurizing mode, can be shortened more effectively. As a result, the injection depth, which is brought about by the syringe 1, can be easily adjusted in the direction in which the injection depth is made shallower.

The predetermined gas, which is generated from the gas generating agent 30, may be also brought in contact with the metal member 16. However, when the predetermined gas is generated, the metal member 16 has been already in such a state that the temperature thereof is raised by the combustion product. Therefore, the thermal energy (heat energy) of the predetermined gas is not uselessly deprived by the metal member 16. That is, the metal member 16 does not inhibit the pressurization to be applied to the injection solution by the second pressurizing mode. The pressure, which is brought about in the second pressurizing mode in accordance with the combustion of the gas generating agent 30, is transmitted to the side of the piston 6 without causing any loss of energy.

According to the fact as described above, it is considered that the effective diffusion of the injection solution is also realized in the skin structure by the pressure control based on the first pressurizing mode and the second pressurizing mode in the syringe 1 shown in FIG. 7. In the foregoing embodiment, the pressure is transmitted by means of the through-hole 17. However, in place thereof, it is also allowable to adopt such a construction that a groove or grooves is/are formed on the surface of the metal member 16 and the pressure in the combustion chamber 9 is transmitted to the side of the piston 6 via the groove or grooves.

Other Examples

According to the syringe 1 of the present invention, for example, cultured cells or stem cells can be seeded or inoculated with respect to cells or scaffold tissue (scaffold) as the injection target in the field of the regenerative medicine, other than the case in which the injection solution is injected into the skin structure as described above. For example, as described in JP2008-206477A, it is possible to inject, by the syringe 1, cells which may be appropriately determined by those skilled in the art depending on the portion subjected to the transplantation and the purpose of the cell regeneration, for example, endothelial cell, endothelial precursor Cell, myeloid cell, preosteoblast, chondrocyte, fibroblast, skin cell, muscle cell, liver cell, kidney cell, intestinal tract cell, and stem cell, as well as every cell considered in the field of the regenerative medicine. More specifically, a solution (cell suspension) containing the cells to be seeded or inoculated as described above is accommodated in the through-hole 14 by using the sealing members 7, 8, for which the pressurization is performed in accordance with the pressure transition based on the first pressurizing mode and the second pressurizing mode as described above. Accordingly, the predetermined cells are injected and transplanted to the portion subjected to the transplantation.

Further, the syringe 1 according to the present invention can be also used to deliver DNA or the like, for example, to cells or scaffold tissue (scaffold) as described in JP2007-525192W. In this case, it is possible to suppress the influence exerted, for example, on cells themselves or scaffold tissue (scaffold) itself when the syringe 1 according to the present invention is used, as compared with when the delivery is performed by using any needle. Therefore, it is affirmed that the use of the syringe 1 according to the present invention is more preferred.

Further, the syringe 1 according to the present invention is also preferably used, for example, when various genes, cancer suppressing cells, or lipid envelops are directly delivered to the objective tissue and when the antigen gene is administered in order to enhance the immunity against the pathogen. Other than the above, the syringe 1 can be also used, for example, for the field of the medical treatment for various diseases (field as described, for example, in JP2008-508881 and JP2010-503616) and the field of the immunological medical treatment (immunotherapy) (field as described, for example, in JP2005-523679). The field, in which the syringe 1 is usable, is not intentionally limited.

PARTS LIST

1: syringe, 2: main syringe body, 4: nozzle, 5: holder, 6: piston, 7, 8: sealing member, 9: combustion chamber, 10: recess, 11: flow passage, 20: initiator, 22: ignition charge, 30; gas generating agent.

The invention claimed is:

1. A syringe for injecting an injection objective substance into an injection target area of a living body without using an injection needle, the syringe comprising: an ignition device which includes an ignition charge containing a fuel component and an oxidizing agent component; a combustion chamber into which a combustion product produced by a reaction of the fuel component and the oxidizing agent component during combustion of the ignition charge is allowed to flow and which accommodates a gas generating agent that is combustible by the combustion product to generate a predetermined gas; an enclosing unit which encloses the injection objective substance; a pressurizing unit which is constructed to pressurize the injection objective substance enclosed in the enclosing unit by means of a pressure in the combustion chamber; a flow passage unit which defines a flow passage so that the injection objective substance, which is pressurized by the pressurizing unit, is allowed to inject to the injection target area of the living body, and a cooling member which is arranged in the combustion chamber so that the cooling member can be brought in contact with the combustion product produced by the combustion of the ignition charge to cool the combustion product, the cooling member having a side surface of a cylindrical outer shape including a plurality of through-holes or mesh holes and a hollow chamber, the hollow chamber defining at least a portion of the flow passage, the side surface of the cooling member being in a direction in which the combustion product flows into the combustion chamber such that the whole combustion product is not cooled to an ordinary temperature by the cooling member, the ordinary temperature being different from and lower than a high temperature which is provided immediately after the combustion reaction of the fuel component, wherein, the fuel component and the oxidizing agent component contained in the ignition charge are determined so that any component, which behaves as a gas, is excluded from the combustion product when the combustion product is at the ordinary temperature in the case where the fuel component and the oxidizing agent component are mixed at a stoichiometric ratio and combusted.

2. The syringe according to claim 1, wherein the pressurizing unit has:
a first pressurizing mode in which a pressure applied to the injection objective substance in the pressurizing unit is raised to a first peak pressure in order to allow the injection objective substance to penetrate through a surface of the injection target area, and then the pressure applied to the injection objective substance is lowered to a waiting pressure; and
a second pressurizing mode in which the injection objective substance having the waiting pressure is pressurized so that the pressure applied to the injection objective substance is raised to a second peak pressure to inject a predetermined injection amount of the injection objective substance.

3. The syringe according to claim 1, wherein the cooling member is formed of a material made of metal.

4. The syringe according to claim 1, wherein: the cooling member is a metal member and the metal member is provided so that the pressure, which is brought about by the predetermined gas and the combustion product produced in the combustion chamber, is transmitted to the injection objective substance.

5. The syringe according to claim 1, wherein the ignition charge is any one of explosive charges of an explosive charge containing zirconium and potassium perchlorate, an explosive charge containing titanium hydride and potassium perchlorate, an explosive charge containing titanium and potassium perchlorate, an explosive charge containing aluminum and potassium perchlorate, an explosive charge containing aluminum and bismuth oxide, an explosive charge containing aluminum and molybdenum oxide, an explosive charge containing aluminum and copper oxide, and an explosive charge containing aluminum and iron oxide, or an explosive charge composed of a combination of a plurality of the foregoing explosive charges.

6. The syringe according to claim 1, wherein the cooling member is arranged along a side wall of the combustion chamber so that a central axis thereof in the extending direction is mutually overlapped with that of the combustion chamber.

\* \* \* \* \*